(12) United States Patent
Heiser et al.

(10) Patent No.: US 7,625,939 B2
(45) Date of Patent: Dec. 1, 2009

(54) CYCLOPROPYL-FUSED PYRROLIDINE DERIVATIVES AS DIPEPTIDYL PEPTIDASE IV INHIBITORS

(75) Inventors: Ulrich Heiser, Halle/Saale (DE); Andre J. Niestroj, Sennewitz (DE); Ulf-Torsten Gaertner, Halle/Saale (DE); Hans-Ulrich Demuth, Halle/Saale (DE)

(73) Assignee: Probiodrug AG, Halle/Saale (DE)

( * ) Notice: Subject to any disclaimer, the term of this patent is extended or adjusted under 35 U.S.C. 154(b) by 0 days.

(21) Appl. No.: 12/120,595

(22) Filed: May 14, 2008

(65) Prior Publication Data

US 2008/0293618 A1 Nov. 27, 2008

Related U.S. Application Data

(63) Continuation-in-part of application No. PCT/EP2006/068404, filed on Nov. 13, 2006.

(60) Provisional application No. 60/736,359, filed on Nov. 14, 2005.

(51) Int. Cl.
*A61K 31/40* (2006.01)
*C07D 209/00* (2006.01)

(52) U.S. Cl. .................. 514/408; 514/412; 514/64; 514/75; 548/405; 548/412; 548/416

(58) Field of Classification Search .................. 548/405, 548/412, 416; 514/408, 412
See application file for complete search history.

(56) References Cited

U.S. PATENT DOCUMENTS 6,303,661 B1  10/2001  Demuth

FOREIGN PATENT DOCUMENTS

| DE | 19828114 | 1/2000 |
|---|---|---|
| DE | 19828113 | 11/2008 |
| WO | 9529691 | 11/1995 |
| WO | 9740832 | 11/1997 |
| WO | 9938501 | 8/1999 |
| WO | 9961431 | 12/1999 |
| WO | 9967228 | 12/1999 |
| WO | 9967279 | 12/1999 |
| WO | 0119866 | 3/2001 |
| WO | 0168603 | 9/2001 |
| WO | 0204610 | 1/2002 |
| WO | 0231134 | 4/2002 |
| WO | 0234900 | 5/2002 |
| WO | 03002593 | 1/2003 |
| WO | 2005047297 | 5/2005 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Morissette et al. Advanced Drug Delivery Reviews 2004, 56, 275-300.*
Vippagunta, Sudha R. "Crystalline Solids." Advanced Drug Delivery Reviews 48(2001): 3-26.*
Design of Prodrugs, Ed. H. Bundgaard, Elsevier, 1985.
Sedo and Malik, Dipeptidyl peptidase IV-like molecules: homologous proteins or homologous activities?, Biochimica et Biophysica Acta, 2001, p. 1-10, vol. 36506.
Protective Groups in Organic Chemistry, Ed. JFW McOmie, Plenum Press, 1973.
TW Greene and PGM Wuts, Protective Groups in Organic Synthesis, John Wiley & Sons, 1991.
Report of the Expert Committee on the Diagnosis and Classification of Diabetes Mellitus. Diabetes Care, 2003, p. 5-20, vol. 26.
The Diabetes Ready-Reference Guide for Health Care Professionals, 2000, published by the American Diabetes Association.
Von Hoersten et al., Stereological quantification of carboxyflourescein-labeled rat lung metastasis: a new method for the assessment of natural killer cell activity and tumor adhesion in vivo and in situ, J Immuno Meth, 2000, p. 25-34, vol. 239.

* cited by examiner

*Primary Examiner*—Kamal A Saeed
*Assistant Examiner*—Samantha L Shterengarts
(74) *Attorney, Agent, or Firm*—Sonnenschein Nath & Rosenthal LLP

(57) ABSTRACT

The present invention relates to DP IV-inhibitors of formula (1)

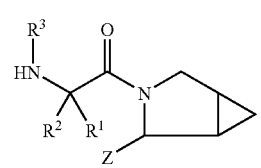

(1)

for the treatment and/or prophylaxis of diseases of mammals including cancer and tumors, metastasis and tumor colonization; and metabolic diseases.

18 Claims, No Drawings

CYCLOPROPYL-FUSED PYRROLIDINE DERIVATIVES AS DIPEPTIDYL PEPTIDASE IV INHIBITORS

CROSS-REFERENCE TO RELATED APPLICATIONS

This application is a continuation-in-part of International Application No. PCT/EP2006/068404 filed Nov. 13, 2006, which claims priority to U.S. Provisional Patent Application No. 60/736,359 filed Nov. 14, 2005. Both of which are incorporated herein by reference to the extent permitted by law.

FIELD OF THE INVENTION

The present invention relates to the area of dipeptidyl peptidase IV inhibition and, more particularly, relates to novel DP IV-inhibitors comprising a boronic acid or phosphonic acid ester moiety and a cyclopropyl-fused proline mimetic, pharmaceutical compositions containing said compounds, and the use of said compounds for inhibiting dipeptidyl peptidase IV and dipeptidyl peptidase IV-like enzymes (e.g. DP II and DP9), together defined as DP IV-activity.

BACKGROUND ART

Dipeptidyl peptidase IV (DP IV) is a serine protease which cleaves N-terminal dipeptides from a peptide chain containing, preferably, a proline residue in the penultimate position. Although the biological role of DP IV in mammalian systems has not been completely established, it is believed to play an important role in neuropeptide metabolism, T-cell activation, attachment of cancer cells to the endothelium and the entry of HIV into lymphoid cells.

DP IV is responsible for inactivating glucagon-like peptide-1 (GLP-1) and glucose-dependent insulinotropic peptide also known as gastric-inhibitory peptide (GIP). GLP-1 is a major stimulator of pancreatic insulin secretion and has direct beneficial effects on glucose disposal. Inhibition of DP IV and DP IV-like enzyme activity has been shown to represent an attractive approach e.g. for treating type 2 diabetes (also: non-insulin-dependent diabetes mellitus or NIDDM), see WO97/40832 and U.S. Pat. No. 6,303,661.

There are a broad variety of DP IV-inhibitors known in the state of the art, and the mechanism of action of these DP IV-inhibitors is mainly by competitive inhibition. WO99/61431 discloses competitive DP IV-inhibitors comprising an amino acid residue and a thiazolidine or pyrrolidine group, and salts thereof, especially L-threo-isoleucyl thiazolidine, L-allo-isoleucyl thiazolidine, L-threo-isoleucyl pyrrolidine, L-allo-isoleucyl pyrrolidine, and salts thereof. WO03/002593 discloses peptide structures useful for competitive modulation of DP IV-activity.

WO95/29691 discloses peptidyl derivatives of diesters of alpha-aminoalkylphosphonic acids, their use in inhibiting serine proteases with chymotrypsin-like, trypsin-like, elastase-like, and dipeptidyl peptidase IV specificity, and their roles as anti-inflammatory agents, anticoagulants, anti-tumor agents, and anti-AIDS agents.

WO99/38501 discloses DP IV-inhibitors which comprise a boronic acid or a phosphorylalkyl residue, and a method of regulating glucose metabolism by administering these compounds to an animal. WO99/38501 does not disclose compounds comprising a cyclopropyl-fused proline mimetic.

WO01/68603 discloses cyclopropyl-fused pyrrolidine-based inhibitors of dipeptidyl peptidase IV and a method of treating diabetes, especially type II diabetes, employing such cyclopropyl-fused pyrrolidines. WO11/68603 does not disclose compounds comprising a boronic acid or a phosphonic acid ester moiety as substituent on the pyrrolidine group.

WO2005/047297 discloses certain heterocyclic boronic acid compounds said to be inhibitors of dipeptidyl peptidase IV.

SUMMARY OF THE INVENTION

The present invention provides novel DP IV-inhibitors which are expected to have improved efficacy in the prophylaxis and treatment of cancer and tumors and the prophylaxis and inhibition of metastasis and tumor colonization, compared with known DP IV-inhibitors.

Further, the present invention provides novel DP IV-inhibitors for the treatment of metabolic diseases, e.g. non-insulin dependent diabetes mellitus (type 2), impaired glucose tolerance, glucosuria, and disturbances of signal action at the cells of the islets of Langerhans and insulin sensitivity in the peripheral tissue in the postprandial phase of mammals, especially in humans.

DETAILED DESCRIPTION OF THE INVENTION

The present invention relates to compounds of formula (1):

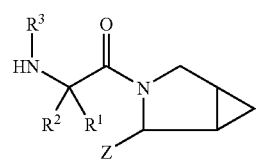

wherein
$R^1$ and $R^2$ are independently selected from hydrogen, alkyl, alkenyl, alkynyl, cycloalkyl, alkylcycloalkyl, heterocyclyl, carbocyclyl, aryl, -alkylaryl, heteroaryl -alkylheteroaryl and an amino acid or a peptide residue;

$R^3$ represents hydrogen;

Z is a group of formula I or II:

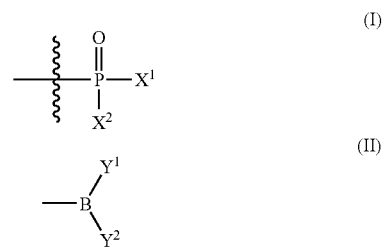

wherein $X^1$ and $X^2$ independently represent $OR^4$;

$R^4$ is selected from the group consisting of hydrogen; alkyl, alkenyl, alkynyl, cycloalkyl any of which aforementioned four groups may optionally be substituted by hydroxy; heterocyclyl, carbocyclyl, aryl, -alkylaryl, heteroaryl and -alkylheteroaryl;

$Y^1$ and $Y^2$ are independently selected from hydroxy, alkoxy, cycloalkyloxy, aryloxy and heteroaryloxy; or $Y^1$ and $Y^2$ are connected to form one of the following cyclic boronic diester groups:

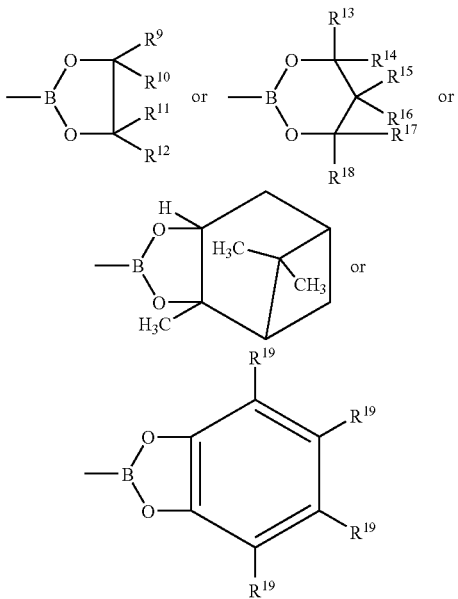

wherein $R^9$-$R^{18}$ are independently hydrogen, alkyl, cycloalkyl or aryl; and each $R^{19}$ group is independently selected from hydrogen, alkyl, aryl, halo, alkoxy, aryloxy, thioalkyl and thioaryl;

in addition when Z represents a group of formula (I):

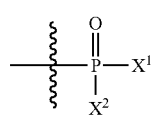

(I)

then $R^3$ may also represent alkyl, alkenyl, alkynyl, cycloalkyl, alkylcycloalkyl, heterocyclyl, carbocyclyl, aryl, -alkylaryl, -alkylheteroaryl, an amino acid or a peptide residue;

and when Z represents a group of formula (I) $R^1$ and $R^3$ may also optionally be connected to form a ring of the structure

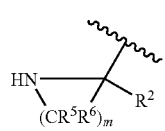

(III)

wherein m is an integer in the range of 2 to 6;

$R^2$ is as defined above;

and $R^1$ and $R^6$ are independently selected from hydrogen, hydroxy, alkoxy, alkyl, alkenyl, alkynyl, cycloalkyl, halo, amino, substituted amino, carbocyclyl, aryl, arylalkyl-, heteroaryl, heteroarylalkyl-, heterocyclyl, alkylcarbonylamino-, arylcarbonylamino-, alkoxycarbonylamino-, aryloxycarbonylamino-, alkoxycarbonyl-, aryloxycarbonyl-, and alkylaminocarbonylamino-;

and pharmaceutically acceptable salts and solvates thereof;

and prodrugs thereof.

The above mentioned compounds may be referred to as "compounds of the invention".

If $R^1$ and $R^3$ are connected then m suitably represents 3 or 4.

Suitably $R^5$ and $R^6$ independently represent hydrogen or methyl, especially hydrogen.

In one embodiment of the invention Z is a group of formula (I):

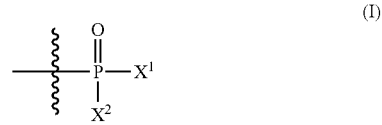

(I)

Suitably, $R^4$ represents hydrogen, lower alkyl or is a substituted phenyl ring, wherein the substituent (for example a single substituent) is selected from the group consisting of halogen, hydroxy and alkoxy. Suitably $R^4$ represents p-halogenophenyl.

Suitably $R^1$, $R^2$ and $R^3$ independently represent hydrogen, alkyl, alkylcycloalkyl or cycloalkyl.

More suitably, when Z represents a group of formula (I) then:

$R^3$ and $R^1$ are hydrogen and $R^2$ is alkyl, alkylcycloalkyl or cycloalkyl; or $R^2$ is hydrogen and $R^1$ is connected to $R^3$ such that the moiety $HR^3N$—$CR^1R^2$—CO— represents the residue of L-proline.

Most suitably, when Z represents a group of formula (I) then $R^3$ and $R^1$ are hydrogen and $R^2$ is lower alkyl.

In a more preferable embodiment, Z is a group of formula (II):

(II)

Suitably $Y^1$ and $Y^2$ both represent hydroxy.

Alternatively $Y^1$ and $Y^2$ independently represent alkoxy, cycloalkyloxy, aryloxy or heteroaryloxy.

When $Y^1$ and $Y^2$ are connected to form a cyclic boronic diester:

Suitably $R^9$-$R^{12}$ are independently hydrogen, methyl, phenyl or cyclohexyl.

Most suitably $R^9$ and $R^{10}$ are independently methyl, phenyl or cyclohexyl (e.g. methyl) and $R^{10}$ and $R^{12}$ are hydrogen.

Suitably $R^{13}$-$R^{18}$ are independently hydrogen, methyl, cyclohexyl or phenyl.

Most suitably $R^{18}$ is $C_{2-6}$ alkyl and $R^{13}$-$R^{17}$ are hydrogen, or $R^{15}$ is $C_{2-6}$ alkyl and $R^3$, $R^4$, $R^6$, $R^{17}$ and $R^{18}$ are hydrogen.

Suitably each $R^{19}$ group is independently selected from hydrogen and alkyl (e.g. methyl).

In one suitable embodiment $Y^1$ and $Y^2$ are connected as a cyclic boronic ester formed from a boronic acid compound of formula (I) and pinanediol.

In another suitable embodiment $Y^1$ and $Y^2$ are connected and together represent —O—$CH_2CH_2$—O— or —O—$CH_2CH_2CH_2$—O—.

When Z represents a group of formula (II) then:

Suitably $R^2$ is hydrogen.

Suitably $R^1$ is $C_{2-6}$ alkyl e.g. butyl or propyl particularly —$CMe_3$, $CHMe_2$ or $CHMeCH_2Me$.

Preferably $R^2$ is hydrogen and $R^1$ is $C_{2-6}$ alkyl e.g. —CMe$_3$, CHMe$_2$ or CHMeCH$_2$Me.

Most preferably the moiety HR$^3$N—CR$^1$R$^2$—CO— represents the residue of L-valine, L-isoleucine or L-(t-butyl) glycine.

Preferred compounds of formula (1) have a molecular weight of less than 1000 Da e.g. less than 600 Da.

DEFINITIONS

The following definitions refer to the whole description and especially to the claims.

As used herein, the term "pharmaceutically acceptable" embraces both human and veterinary use: for example the term "pharmaceutically acceptable" embraces a veterinarily acceptable substance or a substance acceptable in human medicine and health care.

Throughout the description and the claims the expression "acyl", unless specifically limited, denotes a $C_{1-12}$ acyl residue, preferably a $C_{1-8}$ acyl residue and especially preferred a $C_{1-4}$ acyl residue. Examples of acyl include alkanoyl groups mentioned below and benzoyl.

Throughout the description and the claims the expression "alkyl", unless specifically limited, denotes a $C_{1-12}$ alkyl group, preferably a $C_{1-6}$ alkyl group e.g. a $C_{1-4}$ alkyl group. Alkyl groups may be straight chain or branched. Suitable alkyl groups include, for example, methyl, ethyl, propyl (e.g. n-propyl and isopropyl), butyl (e.g. n-butyl, tert-butyl and sec-butyl), pentyl, hexyl, heptyl (e.g. n-heptyl) and octyl (e.g. n-octyl). The expression "alk", for example in the expression "alkoxy", and the expression "alkan", for example in the expression "alkanoyl", should be interpreted in accordance with the definition of "alkyl". Exemplary alkoxy groups include methoxy, ethoxy, butoxy (e.g. n-butoxy), heptyloxy (e.g. n-heptyloxy) and octyloxy (e.g. n-octyloxy). Exemplary alkanoyl (i.e. acyl groups) include ethanoyl (i.e. acetyl), propionyl and butyryl.

"Lower alkyl" refers to an alkyl group having 1-4 carbon atoms (i.e. $C_{1-4}$alkyl) e.g. methyl or ethyl.

The expression "alkenyl", unless specifically limited, denotes a $C_{2-12}$ alkenyl group, preferably a $C_{2-6}$ alkenyl group e.g. a $C_{2-4}$ alkenyl group, which contains at least one double bond at any desired location. Alkenyl groups may be straight chain or branched. Exemplary alkenyl groups include ethenyl, propenyl and butenyl.

If the formation of an E configuration or, respectively, a Z configuration of a double bond in an "alkenyl group" is possible, both the E and Z configuration are comprised in this application.

The expression "alkynyl", unless specifically limited, denotes a $C_{2-12}$ alkynyl group, preferably a $C_{2-6}$ alkynyl group, which contains at least one triple bond at any desired location. Alkynyl groups may be straight chain or branched. Exemplary alkenyl groups include ethynyl, propynyl and butynyl.

Generally, the term "alkynyl group" comprises also compounds having double bonds as well as triple bonds, i.e. "alkeninyl groups", for example having one double bond and, additionally, one triple bond. As an example therefore, the group 4,7-dimethyl-oct-6-en-2-in-1-yl (—CH$_2$—C≡C—CH(CH$_3$)—CH$_2$—CH═C(CH$_3$)$_2$) may be given.

The expression "cycloalkyl", unless specifically limited, denotes a $C_{3-12}$ cycloalkyl group, preferably a $C_{3-8}$ cycloalkyl group. Exemplary cycloalkyl groups include cyclopropyl, cyclobutyl, cyclopentyl, cyclohexyl, cycloheptyl and cyclooctyl. Cycloalkyl groups may be branched in which case the number of carbons indicates the total number of carbons in the moiety.

Examples of alkylcycloalkyl groups include $C_{1-6}$alkyl$C_{1-6}$ cycloalkyl groups such as cyclopentylmethyl- and cyclohexylmethyl-.

Alkyl groups including derivatives such as alkoxy together with alkenyl, alkynyl and cycloalkyl groups may optionally be halogen substituted e.g. substituted by fluoro. For example, halo substituted alkyl groups include trifluoromethyl and halo substituted alkoxy groups include trifluoromethoxy.

By "amino" is meant NH$_2$. Substituted amino groups include amino substituted by alkyl or acyl e.g. NHMe, NMe$_2$ and NHCOMe.

The term "halogen" comprises fluorine (—F), chlorine (—Cl), bromine (—Br), and iodine (—I).

The expression "carbocyclyl", unless specifically limited, denotes a carbocyclic group containing between 3 and 12 carbon atoms, more preferably between 3 and 8 carbon atoms, which may optionally be branched. A carbocyclic group, as used herein, refers to a group other than aryl or cycloalkyl which comprises at least one ring of carbon atoms without heteroatoms. Examples of carbocyclic groups include bridged ring systems (e.g. bicyclo[2.2.1]heptenyl) and partially unsaturated ring systems (e.g. cyclohexenyl). Such groups may be optionally substituted e.g. by alkyl, halo, oxo or hydroxy.

The expression "heterocyclic", unless specifically limited, denotes a cycloalkyl residue or carbocyclic residue, wherein one or more (e.g. 1, 2 or 3) ring atoms are replaced by heteroatoms selected from N, S or O. Exemplary heterocyclic groups containing one hetero atom include pyrrolidine, tetrahydrofuran and piperidine. Exemplary heterocyclic groups containing two hetero atoms include morpholine and piperazine. Such groups may be optionally substituted e.g. by alkyl, halo, oxo or hydroxy.

Further examples of heterocyclic groups include oxirane (oxacyclopropane), aziridine (azacyclopropane), thiirane, oxetane, azetidine, thietane, thiolane, 1,3-dioxolane, thiazolidine, imidazolidine, oxazolidine, pyrazolidine, tetrahydropyran and piperazine. Another example of a heterocycle is urotropine. Other heterocyclic groups include lactams, lactones, cyclic imides and cyclic anhydrides. Examples of substituted heterocyclic groups include 1,1-dioxo-thiolane, N-methyl-piperazine, 2-(N-methyl)-N'-piperazinyl)-ethyl, 4-N-(2'-hydroxyethyl)-1-N-piperazinyl and 2-(N-morpholino)-ethyl.

The expression "aryl", unless specifically limited, denotes a $C_{6-12}$ aryl group, preferably a $C_{6-10}$ aryl group. Aryl groups will contain at least one aromatic ring (e.g. one, two or three rings), but may also comprise partially or fully unsaturated rings. An example of an aryl group with one aromatic ring is phenyl. Examples of aromatic groups with two aromatic rings include naphthyl (e.g. 1-naphthyl-, or 2-naphthyl-). Other aryl groups include 1-anthracenyl-, 2-anthracenyl- and 3-anthracenyl-. Examples of aryl groups which contain partially or fully unsaturated rings include tetralin and indene. A most typical aryl group is phenyl.

The expression "heteroaryl", unless specifically limited, or otherwise defined, denotes as an aryl residue, wherein one or more (e.g. 1, 2, 3, or 4, preferably 1, 2 or 3) ring atoms are replaced by heteroatoms selected from N, S and O or else a 5-membered aromatic ring containing one or more (e.g. 1, 2, 3, or 4, preferably 1, 2 or 3) ring atoms selected from N, S and O. As noted below, heteroaryl groups may optionally be substituted. Exemplary heteroaryl groups include, pyridine (e.g.

2-, 3- or 4-pyridine), pyrimidine, quinoline, pyrrole, furan, thiophene, oxazole, pyrazole, benzodioxolane (benzodioxole), benzodioxane, benzothiophene, benzodioxepine, and thiazole, imidazole (e.g. 1-, 2- or 4-imidazole), isoxazole, isothiazole, 3-pyrazole, 1,2,3-triazole, 1,2,4-triazole, tetrazole, pyridazine, pyrazine, indazole, indole (e.g. 6-indole), benzimidazole, isoquinoline, purine, carbazole and acridine groups.

The aforementioned aryl and heteroaryl groups may, where appropriate, optionally be substituted by one or more (e.g. 1, 2 or 3, preferably 1 or 2) monovalent or multivalent functional groups. Suitable substituent groups include alkyl, cycloalkyl, phenyl, furyl, carbocylyl, heterocyclyl, alkoxy, cycloalkoxy, phenyloxy, furyloxy, carbocyclyloxy, heterocyclyloxy, alkenyloxy, alkynyloxy, alkenyl, alkynyl, alkanoyl, alkoxyalkanoyl, alkoxyalkyl, nitro, —S-alkyl (e.g. methylthio) halo (e.g. fluoro, chloro, bromo and iodo), cyano, hydroxy, —$SO_2$alkyl, —$SO_2$cycloalkyl —$SO_2$heterocyclyl, —$CO_2$H, —$CO_2$alkyl, —$NH_2$, —NHalkyl, —N(alkyl)$_2$ (e.g. dimethylamino), —CO—N(alkyl)$_2$ and —CO—NH(alkyl). Most typical substituent groups are selected from alkyl, alkoxy, halo, nitro and hydroxy.

Examples of substituted aryl groups include 4-fluoro-phenyl, 3-fluoro-phenyl, pentafluoro-phenyl, 4-hydroxyphenyl-, 3-nitro-phenyl-, 4-(trifluoromethyl)-phenyl-, 4-anilinyl-, 2-biphenylyl-, 3-biphenylyl- and 4-biphenylyl-. Examples of substituted heteroaryl groups include N-methyl-2-pyrrolyl, 2-methyl-1-pyrrolyl, 3-methyl-2-pyrrolyl and 3-phenyl-1-pyrrolyl.

Examples of -alkylaryl include phenylmethyl- (i.e. benzyl) and phenylethyl, 2-phenyleth-1-yl, p-tolyl-methyl-, p-tolyl-ethyl-, m-tolyl-methyl-, m-tolyl-ethyl-, o-tolyl-methyl-, o-tolyl-ethyl-, 2-(4-ethyl-phenyl)-eth-1-yl-, 2,3-dimethyl-phenyl-methyl-, 2,4-dimethyl-phenyl-methyl-, 2,5-dimethyl-phenyl-methyl-, 2,6-dimethyl-phenyl-methyl-, 3,4-dimethyl-phenyl-methyl-, 3,5-dimethyl-phenyl-methyl-, 2,4,6-trimethyl-phenyl-methyl-, 2,3-dimethyl-phenyl-ethyl-, 2,4-dimethyl-phenyl-ethyl-, 2,5-dimethyl-phenyl-ethyl-, 2,6-dimethyl-phenyl-ethyl-, 3,4-dimethyl-phenyl-ethyl-, 3,5-dimethyl-phenyl-ethyl-, 2,4,6-trimethyl-phenyl-ethyl-, benzhydryl (i.e. diphenyl-methyl), diphenyl-ethy), trityl (i.e. triphenyl-methyl), triphenyl-ethyl, cumyl (i.e. 1-methyl-1-phenylethyl), 2-ethyl-phenyl-methyl-, 3-ethyl-phenyl-methyl-, 4-ethyl-phenyl-methyl-, 2-ethyl-phenyl-ethyl-, 3-ethyl-phenyl-ethyl-, 4-ethyl-phenyl-ethyl-, 2-fluoro-benzyl, 1-methyl-2-fluoro-phen-6-yl-methyl-, 1-methyl-2-fluoro-phen-4-yl-methyl-, 1-methyl-2-fluoro-phen-6-yl-ethyl-, 1-methyl-2-fluoro-phen-4-yl-ethyl-, 1H-indenyl-methyl-, 2H-indenyl-methyl-, 1H-indenyl-ethyl-, 2H-indenyl-ethyl-, indanyl-methyl-, indan-1-on-2-yl-methyl-, indan-1-on-2-yl-ethyl-, tetralinyl-methyl-, tetralinyl-ethyl-, fluorenyl-methyl-, fluorenyl-ethyl-, dihydronaphthalinyl-methyl-, dihydronaphthalinyl-ethyl-, (4-cyclohexyl)-phenyl-methyl- and (4-cyclohexyl)-phenyl-ethyl.

Examples of -alkylheteroaryl include pyridinylmethyl-, N-methyl-pyrrol-2-methyl-N-methyl-pyrrol-2-ethyl-, N-methyl-pyrrol-3-methyl-, N-methyl-pyrrol-3-ethyl-, 2-methyl-pyrrol-1-methyl-, 2-methyl-pyrrol-1-ethyl-, 3-methyl-pyrrol-1-methyl-, 3-methyl-pyrrol-1-ethyl-, 4-pyridino-methyl-, 4-pyridino-ethyl-, 2-(thiazol-2-yl)-ethyl-, tetrahydroisochinolinyl-methyl-, tetrahydroisochinolinyl-ethyl-, 2-ethyl-indol-1-methyl-, 2-ethyl-indol-1-ethyl-, 3-ethyl-indol-1-methyl-, 3-ethyl-indol-1-ethyl-, 4-methyl-pyridin-2-methyl-, 4-methyl-pyridin-2-yl-ethyl-, 4-methyl-pyridin-3-methyl and 4-methyl-pyridin-3-ethyl.

Stereoisomers:

All possible stereoisomers of the claimed compounds are included in the present invention. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (–)-di-p-toluoyl-d-tartaric acid and/or (+)-di-p-toluoyl-1-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

Pharmaceutically Acceptable Salts:

In view of the close relationship between the free compounds and the compounds in the form of their salts, whenever a compound is referred to in this context, a corresponding salt is also intended, provided such is possible or appropriate under the circumstances.

The pharmaceutically acceptable salt generally takes a form in which a basic side chain of a compound (typically an amine group) is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toulenesulfonic, cyclohexanesulfamic, salicylic, saccharinic and trifluoroacetic acids. All pharmaceutically acceptable acid addition salt forms of the compounds of the present invention are intended to be embraced by the scope of this invention.

Solvates:

Compounds of the invention may form solvates with water (i.e. hydrate) or common organic solvents which are embraced as an aspect of the invention.

Polymorph Crystal Forms:

Furthermore, compounds of the invention (including their salts and solvates) may exist as crystalline solids and all polymorphic forms thereof are included in the present invention.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985 and the patent applications DE 198 28 113, DE 198 28 114, WO99/67228 and WO99/67279 which are fully incorporated herein by reference.

Examples of prodrugs include boronic acid derivatives (i.e. compounds of formula (1) in which $Y^1$ and $Y^2$ are not both hydroxyl) which are converted in vivo (typically following oral administration) by hydrolysis to yield a compound in which $Y^1$ and $Y^2$ both represent hydroxy. Examples include other cyclic boronic diesters besides those compounds described above.

Amino Acids

Examples of amino acids which can be used in the present invention are L- and D-amino acids, N-methyl-amino acids, aza-amino acids; allo- and threo-forms of Ile and Thr, which can, e.g. be α-, β- or ω-amino acids, whereof α-amino acids are preferred.

Examples of amino acids are:
aspartic acid (Asp), glutamic acid (Glu), arginine (Arg), lysine (Lys), histidine (His), glycine (Gly), serine (Ser), cysteine (Cys), threonine (Thr), asparagine (Asn), glutamine (Gln), tyrosine (Tyr), alanine (Ala), proline (Pro), valine (Val), isoleucine (Ile), leucine (Leu), methionine (Met), phenylalanine (Phe), tryptophan (Trp), hydroxyproline (Hyp), beta-alanine (beta-Ala), 2-aminooctanoic acid (Aoa), acetidine-(2)-carboxylic acid (Ace), pipecolic acid (Pip), 3-aminopropionic acid, 4-aminobutyric acid and so forth, alpha-aminoisobutyric acid (Aib), sarcosine (Sar), ornithine (Orn), citrulline (Cit), homoarginine (Har), t-butylalanine (t-butyl-Ala), t-butylglycine (t-butyl-Gly), N-methylisoleucine (N-MeIle), phenylglycine (Phg), cyclohexylalanine (Cha), norleucine (Nle), cysteic acid (Cya) and methionine sulfoxide (MSO), acetyl-Lys, modified amino acids such as phosphoryl-serine (Ser(P)), benzyl-serine (Ser(Bzl)) and phosphoryl-tyrosine (Tyr(P)), 2-aminobutyric acid (Abu), aminoethylcysteine (AECys), carboxymethylcysteine (Cmc), dehydroalanine (Dha), dehydroamino-2-butyric acid (Dhb), carboxyglutaminic acid (Gla), homoserine (Hse), hydroxylysine (Hyl), cis-hydroxyproline (cis Hyp), trans-hydroxyproline (transHyp), isovaline (Iva), pyroglutamic acid (Pyr), norvaline (Nva), 2-aminobenzoic acid (2-Abz), 3-aminobenzoic acid (3-Abz), 4-aminobenzoic acid (4-Abz), 4-(aminomethyl)benzoic acid (Amb), 4-(aminomethyl)cyclohexanecarboxylic acid (4-Amc), Penicillamine (Pen), 2-amino-4-cyanobutyric acid (Cba), cycloalkane-carboxylic acids. Examples of ω-amino acids are e.g.: 5-Ara (a minoraleric acid), 6-Ahx (aminohexanoic acid), 8-Aoc (aminooctanoic acid), 9-Anc (aminovanoic acid), 10-Adc (aminodecanoic acid), 11-Aun (aminoundecanoic acid), 12-Ado (aminododecanoic acid). Further amino acids are: indanylglycine (Igl), indoline-2-carboxylic acid (Idc), octahydroindole-2-carboxylic acid (Oic), diaminopropionic acid (Dpr), diaminobutyric acid (Dbu), naphthylalanine (1-Nal) and (2-Nal), 4-aminophenylalanine (Phe(4-$NH_2$)), 4-benzoylphenylalanine (Bpa), diphenylalanine (Dip), 4-bromophenylalanine (Phe(4-Br)), 2-chlorophenylalanine (Phe(2-Cl)), 3-chlorophenylalanine (Phe(3-Cl)), 4-chlorophenylalanine (Phe(4-Cl)), 3,4-chlorophenylalanine (Phe(3,4-$Cl_2$)), 3-fluorophenylalanine (Phe(3-F)), 4-fluorophenylalanine (Phe(4-F)), 3,4-fluorophenylalanine (Phe(3,4-$F_2$)), pentafluorophenylalanine (Phe($F_5$)), 4-guanidinophenylalanine (Phe(4-guanidino)), homophenylalanine (hPhe), 3-iodophenylalanine (Phe(3-J)), 4-iodophenylalanine (Phe(4-J)), 4-methylphenylalanine (Phe (4-Me)), 4-nitrophenylalanine (Phe(4-$NO_2$)), biphenylalanine (Bip), 4-phosphonomethylphenylalanine (Pmp), cyclohexylglycine (Ghg), 3-pyridinylalanine (3-Pal), 4-pyridinylalanine (4-Pal), 3,4-dehydroproline (A-Pro), 4-ketoproline (Pro(4-keto)), thioproline (Thz), isonipecotic acid (Inp), 1,2,3,4,-tetrahydroisoquinolin-3-carboxylic acid (Tic), propargylglycine (Pra), 6-hydroxynorleucine (NU(6-OH)), homotyrosine (hTyr), 3-iodotyrosine (Tyr(3-J)), 3,5-diiodotyrosine (Tyr(3,5-$J_2$)), methyltyrosine (Tyr(Me)), 2',6'-dimethyltyrosine (Dmt), 3-$NO_2$-tyrosine (Tyr(3-$NO_2$)), phosphotyrosine (Tyr($PO_3H_2$)), alkylglycine, 1-aminoindane-1-carboxylic acid, 2-aminoindane-2-carboxylic acid (Aic), 4-amino-methylpyrrol-2-carboxylic acid (Py), 4-amino-pyrrolidine-2-carboxylic acid (Abpc), 2-aminotetraline-2-carboxylic acid (Atc), diaminoacetic acid (Gly($NH_2$)), diaminobutyric acid (Dab), 1,3-dihydro-2H-isoinole-carboxylic acid (Disc), homocyclohexylalanine (hCha), homophenylalanine (hPhe or H of), trans-3-phenyl-azetidine-2-carboxylic acid, 4-phenyl-pyrrolidine-2-carboxylic acid, 5-phenyl-pyrrolidine-2-carboxylic acid, 3-pyridylalanine (3-Pya), 4-pyridylalanine (4-Pya), styrylalanine, tetrahydroisoquinoline-1-carboxylic acid (Tiq), 1,2,3,4-tetrahydronorharmane-3-carboxylic acid (Tpi) and β-(2-thienryl)-alanine (Tha). Preferred amino acids are the 20 natural L-amino acids.

Peptides

"Peptide(s)" or "peptide residue(s)" are selected from dipeptides to decapeptides, preferred are dipeptides, tripeptides, tetrapeptides and pentapeptides. The amino acids for the formation of the "peptides" can be selected from those listed above.

Aza-Amino Acid

An "aza-amino acid" is defined as an amino acid where the chiral α-CH group is replaced by a nitrogen atom, whereas an "aza-peptide" is defined as a peptide, in which the chiral α-CH group of one or more amino acid residues in the peptide chain is replaced by a nitrogen atom.

Other Amino Acid Substitutions

Other amino acid substitutions for those encoded in the genetic code can also be included in peptide compounds within the scope of the invention and can be classified within this general scheme. Proteinogenic amino acids are defined as natural protein-derived α-amino acids. Non-proteinogenic amino acids are defined as all other amino acids, which are not building blocks of common natural proteins.

Mimetics

"Mimetics" in relation to peptides (or proteins) are compounds which have a secondary structure like a peptide and optionally further structural characteristics; their mode of action is largely similar or identical to the mode of action of the native peptide; however, their activity (e.g. as an antagonist or inhibitor) can be modified as compared with the native peptide, especially vis à vis receptors or enzymes. Moreover, they can imitate the effect of the native peptide (agonist). Examples of peptide mimetics are scaffold mimetics, non-peptidic mimetics, peptoides, peptide nucleic acids, oligopyrrolinones, vinylogpeptides and oligocarbamates. For the definitions of these peptide mimetics see Lexikon der Chemie, Spektrum Akademischer Verlag Heidelberg, Berlin, 1999. The aim for using these mimetic structures is increasing the activity, increasing the selectivity to decrease side effects, protect the compound against enzymatic degradation for prolongation of the effect.

The terms "$K_I$" and "$K_D$" are binding constants, which describe the binding of an inhibitor to and the subsequent release from an enzyme. Another measure is the "$IC_{50}$" value, which reflects the inhibitor concentration, which at a given substrate concentration results in 50% enzyme activity.

The term "DP IV-inhibitor" or "dipeptidyl peptidase IV inhibitor" is generally known to a person skilled in the art and means enzyme inhibitors, which inhibit the catalytic activity of DP IV or DP IV-like enzymes.

"DP IV-activity" is defined as the catalytic activity of dipeptidyl peptidase IV (DP IV) and DP IV-like enzymes. These enzymes are post-proline (to a lesser extent post-alanine, post-serine or post-glycine) cleaving serine proteases found in various tissues of the body of a mammal including kidney, liver, and intestine, where they remove dipeptides from the N-terminus of biologically active peptides with a high specificity when proline or alanine form the residues that are adjacent to the N-terminal amino acid in their sequence.

DP IV-Like Enzymes

Among the rare group of proline-specific proteases, DPIV was originally believed to be the only membrane-bound enzyme specific for proline as the penultimate residue at the amino-terminus of the polypeptide chain. However, other molecules, even structurally non-homologous with the DPIV but bearing corresponding enzyme activity, have been identified recently. DPIV-like enzymes, which are identified so far, are e.g. fibroblast activation protein α, dipeptidyl peptidase IV β, dipeptidyl aminopeptidase-like protein, N-acetylated α-linked acidic dipeptidase, quiescent cell proline dipeptidase, dipeptidyl peptidase II, attractin and dipeptidyl peptidase IV related protein (DPP 8), and are described in the review article by Sedo & Malik (Sedo & Malik, Dipeptidyl peptidase IV-like molecules: homologous proteins or homologous activities? Biochimica et Biophysica Acta 2001, 36506: 1-10).

Further DPIV-like enzymes are disclosed in WO01/19866, WO02/04610, WO02/34900 and WO02/31134. WO01/19866 discloses novel human dipeptidyl aminopeptidase (DPP8) with structural und functional similarities to DPIV and fibroblast activation protein (FAP). WO02/04610 provides reagents, which regulate human dipeptidyl peptidase IV-like enzyme and reagents which bind to human dipeptidyl peptidase IV-like enzyme gene product. These reagents can play a role in preventing, ameliorating, or correcting dysfunctions or diseases including, but not limited to, tumors and peripheral and central nervous system disorders including pain and neurodegenerative disorders. The dipeptidyl peptidase IV-like enzyme of WO02/04610 is well known in the art. In the Gene Bank data base, this enzyme is registered as KIAA1492 (registration in February 2001, submitted on Apr. 4, 2000, AB040925). WO02/34900 discloses a dipeptidyl peptidase 9 (DPP9) with significant homology with the amino acid sequences of DPIV and DPP8. WO02/31134 discloses three DPIV-like enzymes, DPRP1, DPRP2 and DPRP3. Sequence analysis revealed, that DPRP1 is identical to DPP8, as disclosed in WO01/19866, that DPRP2 is identical to DPP9 and that DPRP3 is identical to KIAA1492 as disclosed in WO02/04610.

Anti-Tumor Drug

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P1-(DDD)), interferons and radioactive agents. As used herein, "a cytotoxin or cytotoxic agent" means any agent that is detrimental to cells. Examples include taxanes, e.g. taxol and taxotere, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, FU, cisplatin, adriamycin, oxaliplatin, cyclophosphamide, EGF and VGF inhibitors and puromycin and analogs or homologs thereof.

Subject

The term "subject" as used herein, refers to an animal, preferably a mammal, most preferably a human, who has been the object of treatment, observation or experiment.

Therapeutically Effective Amount

The term "therapeutically effective amount" as used herein, means that amount of active compound or pharmaceutical agent that elicits the biological or medicinal response in a tissue system, animal or human, being sought by a researcher, veterinarian, medical doctor or other clinician, which includes alleviation of the symptoms of the disease or disorder being treated.

As used herein, the term "composition" is intended to encompass a product comprising the claimed compounds in therapeutically effective amounts, as well as any product which results, directly or indirectly, from combinations of the claimed compounds.

General Synthesis Scheme

Compounds of the invention may generally be prepared by the following routes:

Scheme 1 (for preparation of compounds of formula (1) in which Z represents group (II)):

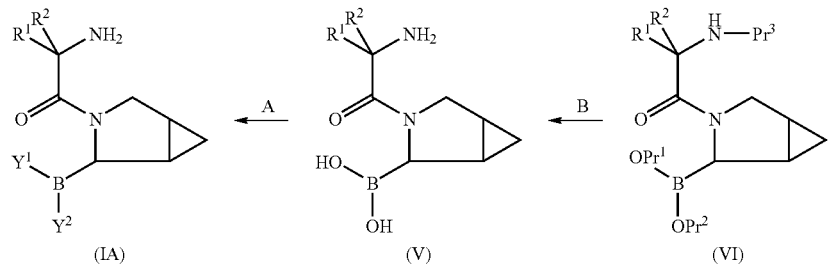

Pr$^1$ and Pr$^2$ represent protecting groups e.g. with an organic diol such as (1S,2S,3R,5S)-pinanediol. Within the scheme it may also be preferred to protect the amine functions.

Step E is a boronation reation. It may, for example, be undertaken through a lithiation reaction performed on a compound of formula (X) involving e.g. secBuLi catalysed with TMEDA and then treating with a boron containing reagent such as B(OMe)$_3$. This reaction is suitably conducted at low temperature e.g. −70° C. for several hours. Preferably the ring amine is previously protected by treatment with Boc, Step D involves protecting the boron function. Suitably it is protected by treatment with an organic diol such as (1S,2S, 3R,5S)-pinanediol.

Step C is a conventional condensation reaction which suitably involves using the compound of formula (VII) in activated form. Compounds of formula (VII) are typically employed in activated form e.g. as an activated ester or anhydride. The amine function of compounds of formula (VII) is suitably protected (Pr$^3$) e.g. by Boc.

Step B is a deprotection reaction which will be appropriate for the protecting group employed. The Boc-protection group is removed by acid. (1S,2S,3R,5S)-pinandiol can be removed by treatment with phenylboronic acid under acidic aqueous conditions, the resulting cyclic boronate is isolated after ion exchange conditions and brought to the open chain ammonium form by adding acid (e.g. MeSO$_3$H).

Step A is an optional step employed when Y$^1$ and Y$^2$ do not both represent OH. Suitable reagents e.g. alcohols and conditions will be known to a person skilled in the art.

Scheme 2 (for preparation of compounds of formula (1) in which Z represents group (I)):

Step H involves treating the compound of formula (X) to yield a trimer (X)$_3$.

Step G involves treating the compound (X)$_3$ with HPO (OR$^4$)$_2$ under elevated temperature.

Step F may be performed in an analogous manner to Step C above.

Compounds of formula (1) wherein R$^3$ does not represent hydrogen may be prepared by reacting a corresponding compound of formula 1 in which R$^3$ does represent hydrogen (prepared e.g. as above) with a suitable reagent under conventional conditions. Alternative the appropriate derivative of the compound of formula (VII) may be used in Scheme 2.

Compounds of formula (X) and (VII) are either known or may be prepared by conventional methods known per se. For example compounds of formula (X) may be prepared by the following general process:

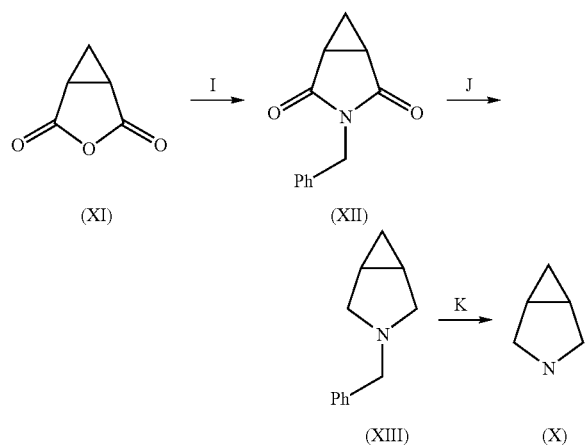

Compounds of formula (XI) are either known or may be prepared by conventional methods known per se.

Step I involved treatment of compound (XI) with benzylamine at elevated temperature.

Step J involves use of an appropriate reducing agent e.g. LiAlH$_4$.

Step K involves deprotection of the amine group, typically be reduction over Pd/C.

Further and specific details of suitable conditions and reagents to be employed in Schemes 1 and 2 may be gleaned by reference to the examples.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991, fully incorporated herein by reference. The protecting groups may be removed at a convenient subsequent stage using methods known from the art.

Medical Use/Methods of Treatment

The present invention provides compounds of the invention for the use as a pharmaceutical.

Cancer: The present invention may be used for treatment and/or prophylaxis in mammals, preferably humans, of cancer and tumors and the prophylaxis and inhibition of metastasis and tumor colonization including, but not limited to, adenocarcinomas, melanomas, lymphomas, sarcomas, leukemias, and different organ tumors like lung, breast, ovarian, head and/or neck, prostate, cervical, endometrial, colorectal, gastric, liver, fallopian tubes, esophagus, small intestine, pancreas, kidney, adrenal, vaginal, vulvar, brain and testicular tumors.

The following further diseases in mammals, preferably humans, may be treated using the compounds of the present invention:

Metabolic diseases like impaired glucose tolerance, glucosuria, hyperlipidemia, metabolic acidosis, diabetes mellitus, non-insulin dependent diabetes mellitus, diabetic neuropathy and nephropathy and of sequelae caused by diabetes mellitus; high blood pressure and disturbance of signal action at the cells of the islets of Langerhans and insulin sensitivity in the peripheral tissue in the postprandial phase; the metabolism-related hypertension and cardiovascular sequelae caused by hypertension;

Conditions, characteristic for the prediabetic state: pathological states, selected from the group consisting of impaired glucose tolerance (IGT), impaired fasting glucose (IFG) and impaired glucose metabolism (IGM);

Dermal diseases like skin diseases and diseases of the mucosae;

Immune and autoimmune disorders, multiple sclerosis, and inflammatory conditions; arthritis; obesity; allograft transplantation;

Neuronal disorders as well as psychosomatic, neuropsychiatric and depressive illnesses, such as anxiety, depression, sleep disorders, chronic fatigue, schizophrenia, epilepsy, nutritional disorders, spasm and chronic pain.

The indications above refer each to both acute and chronic form of the disease.

Further, the following diseases may be treated by the compounds of the present invention:

diabetic neuropathy and nephropathy and of sequelae caused by diabetes mellitus in mammals; metabolism-related hypertension and cardiovascular sequelae caused by hypertension in mammals; for the prophylaxis or treatment of skin diseases and diseases of the mucosae, autoimmune diseases and inflammatory conditions, and for the prophylaxis or treatment of psychosomatic, neuropsychiatric and depressive illness, and neurodegenerative diseases such as anxiety, depression, sleep disorders, chronic fatigue, schizophrenia, epilepsy, nutritional disorders, spasm, and chronic pain.

The DP IV-inhibitors of the present invention are preferably used for the treatment of cancer and/or prevention of metastasis.

More preferably, the inhibitors of the present invention are useful for the treatment of diabetes mellitus, especially non-insulin dependent diabetes (NIDDM) or type 2 diabetes and conditions associated with diabetes mellitus.

Classification of Diabetes

Clinical diabetes may be divided into four general subclasses, including (1) type 1 (caused by beta cell destruction and characterized by absolute insulin deficiency) (2) type 2 (characterized by insulin resistance and relative insulin deficiency (3) other specific types of diabetes (associated with various identifiable clinical conditions or syndromes) and (4) gestational diabetes mellitus. In addition to these clinical categories, two conditions—impaired glucose tolerance and impaired fasting glucose—refer to a metabolic state intermediate between normal glucose homeostasis and overt diabetes. These conditions significantly increase the later risk of diabetes mellitus and may in some instances be part of its natural history. It should be noted that patients with any form of diabetes might require insulin treatment at some point.

Type 2 Diabetes Mellitus

Type 2, by far the most common form of the disease, is found in over 90% of the diabetic patient population. These patients retain a significant level of endogenous insulin secretory capacity. However, insulin levels are low relative to the magnitude of insulin resistance and ambient glucose levels. Type 2 patients are not dependent on insulin for immediate survival and ketosis rarely develops, except under conditions of great physical stress. Nevertheless, these patients may require insulin therapy to control hyperlgycemia. Type 2 diabetes typically appears after the age of 40 years, has a high rate of genetic penetrance unrelated to HLA genes, and is associated with obesity. The clinical features of type 2 diabetes may be mild (fatigue, weakness, dizziness, blurred vision, or other non-specific complaints may dominate the picture) or may be tolerated for many years before the patient seeks medical attention. Moreover, if the level of hyperglycemia is insufficient to produce symptoms, the disease may become evident only after complications develop.

Diagnosis

The diagnosis of diabetes is usually straightforward when the classic symptoms of polyuria, polydipsia, and weight loss are present. All that is required is a random plasma glucose measurement from venous blood that is 200 mg/dL or greater. If diabetes is suspected but not confirmed by a random glucose determination, the screening test of choice is overnight fasting plasma glucose level. The diagnosis is established if fasting is equal to or greater than 126 mg/dL on at least two separate occasions.

Related Conditions

Impaired Glucose Tolerance and Impaired Fasting Glucose

Impaired glucose tolerance (IGT) and impaired fasting glucose (IFG) are terms applied to individuals who have glucose levels that are higher than normal, (under fed or fasting conditions, respectively) but lower than those accepted as diagnostic for diabetes mellitus. Both conditions are associated with an increased risk for cardiovascular disease, but do not produce the classic symptoms or the microvascular and neuropathic complications associated with diabetes mellitus. In a subgroup of patients (about 25 to 30%), however, type 2 diabetes eventually develops.

Impaired Glucose Metabolism

Impaired Glucose Metabolism (IGM) is defined by blood glucose levels that are above the normal range but are high enough to meet the diagnostic criteria for type 2 diabetes mellitus. The incidence of IGM varies from country to country, but usually occurs 2-3 time more frequently than overt diabetes. Until recently, individuals with IGM were felt to be pre-diabetics, but data from several epidemiological studies argue that subjects with IGM are heterogeneous with respect to their risk of diabetes and their risk of cardiovascular morbidity and mortality. The data suggest that subjects with IGM, in particular, those with impaired glucose tolerance (IGT), do not always develop diabetes, but whether they are diabetic or not, they are, nonetheless, at high risk for cardiovascular morbidity and mortality. Among subjects with IGM, about 58% have Impaired Glucose tolerance (IGT), another 29% have impaired fasting glucose (IFG), and 13% have both abnormalities (IFG/IGT). As discussed above, IGT is characterized by elevated post-prandial (post-meal) hyperglycemia while IFG has been defined by the ADA (American Diabetes Association) on the basis of fasting glycaemic values.

The categories of (a) normal glucose tolerance (NGT), (b) impaired glucose metabolism (IGM) and (c) overt type 2 diabetes mellitus are periodically revised and adopted by the Expert Committee of the American Diabetes Association (ADA). The actual values as defined in "Report of the Expert Committee on the Diagnosis and Classification of Diabetes Mellitus. Diabetes Care (26) 1, 2003, 5-20" and "The Diabetes Ready-Reference Guide for Health Care Professionals, 2000, published by the American Diabetes Association" are:

a) Normal Glucose Tolerance (NGT)=fasting glucose level<6.1 mmol/L or less than 110 mg/dl and a 2 h post-prandial glucose level of <7.8 mmol/L or <140 mg/dl.

b) Impaired Glucose Metabolism (IGM) is impaired fasting glucose (IFG) defined as IFG=fasting glucose level of 6.1-7.0 mmol/L or 110-126 mg/dl and/or impaired glucose tolerance (IGT)=a 2 h post-prandial glucose level (75 g OGTT) of 7.8-11.1 mmol/L or 140-200 mg/dl).

c) Type 2 diabetes=fasting glucose of greater than 7 mmol/L or 126 mg/dl or a 2 h post-prandial glucose level (75 g OGTT) of greater than 11.1 mmol/L or 200 mg/dl.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

Accordingly, the compounds and combinations of the present invention are especially useful for the treatment of pathological states, selected from the group consisting of IGT, IFG and IGM.

In particular, the present invention provides the use of compounds of the invention for the preparation of a medicament for the treatment and/or prophylaxis of diseases of mammals selected from the group of:

(i) cancer and tumors, metastasis and tumor colonization;

(ii) metabolic diseases in humans, including non-insulin dependent diabetes mellitus (type 2), impaired glucose tolerance, glucosuria, and disturbances of signal action at the cells of the islets of Langerhans and insulin sensitivity in the peripheral tissue in the postprandial phase of mammals, especially in humans; and (iii) conditions characteristic of the prediabetic state, selected from the group consisting of IGT, IFG and IGM.

Additionally, the present invention provides a method of treatment of diseases of mammals selected from the group consisting of:

(i) cancer and tumors, metastasis and tumor colonization;

(ii) metabolic diseases in humans, including non-insulin dependent diabetes mellitus (type 2), impaired glucose tolerance, glucosuria, and disturbances of signal action at the cells of the islets of Langerhans and insulin sensitivity in the peripheral tissue in the postprandial phase of mammals, especially in humans; and (iii) conditions characteristic of the prediabetic state, selected from the group consisting of IGT, IFG and IGM;

comprising administering a therapeutically active amount of a compound of the invention or a pharmaceutical composition containing a compound of the invention to said mammals, wherein the mammal is preferably a human.

Furthermore, the present invention provides the use of compounds of the invention for the preparation of a medicament for the treatment and/or prophylaxis of:

(i) cancer and tumors, metastasis and tumor colonization; and (ii) metabolic diseases in humans, including non-insulin dependent diabetes mellitus (type 2), impaired glucose tolerance, glucosuria, and disturbances of signal action at the cells of the islets of Langerhans and insulin sensitivity in the peripheral tissue in the postprandial phase of mammals, especially in humans.

Additionally, the present invention provides a method of treatment of diseases of mammals selected from the group consisting of:

(i) cancer and tumors, metastasis and tumor colonization; and (ii) metabolic diseases in humans, including non-insulin dependent diabetes mellitus (type 2), impaired glucose tolerance, glucosuria, and disturbances of signal action at the cells of the islets of Langerhans and insulin sensitivity in the peripheral tissue in the postprandial phase of mammals, especially in humans;

comprising administering a therapeutically active amount of a compound of the invention or a pharmaceutical composition containing a compound of the invention to said mammals, wherein the mammal is preferably a human.

Pharmaceutical Combinations

In a preferred embodiment, the present invention provides a composition, preferably a pharmaceutical composition, comprising at least one DP IV-inhibitor of formula 1, optionally in combination with at least one anti-tumor drug selected from the group consisting of cytotoxins and agents such as antimetabolites, alkylating agents, anthracyclines, antibiotics, antimitotic agents, procarbazine, hydroxyurea, asparaginase, corticosteroids, mytotane (O,P1-(DDD)), interferons and radioactive agents. As used herein, "a cytotoxin or cytotoxic agent" means any agent that is detrimental to cells. Examples include taxanes, e.g. taxol and taxotere, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, FU, cisplatin, adriamycin, oxaliplatin, cyclophosphamide, EGF and VGF inhibitors and puromycin and analogs or homologs thereof.

In a further preferred embodiment, the present invention provides a composition, preferably a pharmaceutical composition, comprising at least one compound of the invention, optionally in combination with at least one agent selected from the group consisting of:
  (a) other DP IV inhibitors;
  (b) insulin sensitizers selected from the group consisting of
    (i) PPAR agonists e.g. PPARγ agonists,
    (ii) biguanides, and
    (iii) protein tyrosin phosphatase-1B (PTP-1B) inhibitors;
  (c) insulin and insulin mimetics;
  (d) sulfonylureas and other insulin secretagogues;
  (e) α-glucosidase inhibitors;
  (f) glucagon receptor agonists;
  (g) GLP-1; GLP-1 mimetics, e.g. N,N-2211 (liraglutide), and GLP-1 receptor agonists;
  (h) GLP-2; GLP-2 mimetics, e.g. ALX-0600 (teduglutide) and GLP-2 receptor agonists;
  (i) exendin-4 and exendin-4 mimetics, e.g. exenatide (AC-2993, synthetic exendin-4);
  (j) GIP, GIP mimetics, and GIP receptor agonists;
  (k) PACAP, PACAP mimetics, and PACAP receptor δ agonists;
  (l) cholesterol lowering agents selected from the group consisting of
    (i) HMG-CoA reductase inhibitors,
    (ii) sequestrants,
    (iii) nicotinyl alcohol, nicotinic acid and salts thereof,
    (iv) PPARα agonists,
    (v) PPARα/γ dual agonists,
    (vi) inhibitors of cholesterol absorption,
    (vii) acyl CoA:cholesterol acyltransferase inhibitors, and
    (viii) antioxidants;
  (m) PPARδ agonists;
  (n) antiobesity compounds;
  (o) an ileal bile acid transporter inhibitor; and
  (p) anti-inflammatory agents.

In a further specific embodiment there is provided a composition, preferably a pharmaceutical composition, comprising at least one compound of the invention, optionally in combination with at least one anti-diabetic agent (e.g. selected from insulin sensitizers, for example PPAR agonists, biguanides and PTB-1B inhibitors).

In a further embodiment, the present invention provides a composition, preferably a pharmaceutical composition, comprising at least one compound of the invention, optionally in combination with at least one agent according to any one of the embodiments of the present invention mentioned above,
  in combination with a gene therapeutic expression system for GLP-1 comprising a viral vector comprising:
    (a) a polynucleotide sequence encoding GLP-1 (glucagon like peptide-1); and
    (b) a polynucleotide sequence encoding a signal sequence upstream of (a); and
    (c) a polyadenylation signal downstream of (a); and
    (d) a polynucleotide sequence encoding a proteolytic cleavage site located between the polynucleotide sequence encoding GLP-1 and the polynucleotide sequence encoding the signal sequence; and
    (e) wherein the expression of GLP-1 underlies a constitutive promoter or is controlled by a regulatable promoter;
    (f) wherein, optionally, the viral vector comprises a polynucleotide sequence encoding GIP (glucose dependent insulinotropic peptide);
    (g) wherein, optionally, the viral vector is encompassed by a mammalian cell;

and/or
  in combination with a gene therapeutic expression system for GIP comprising a viral vector comprising:
    (a) a polynucleotide sequence encoding GIP (glucose dependent insulinotropic peptide); and
    (b) a polynucleotide sequence encoding a signal sequence upstream of (a); and
    (c) a polyadenylation signal downstream of (a); and
    (d) a polynucleotide sequence encoding a proteolytic cleavage site located between the polynucleotide sequence encoding GIP and the polynucleotide sequence encoding the signal sequence; and
    (e) wherein the expression of GIP underlies a constitutive promoter or is controlled by a regulatable promoter;
    (f) wherein, optionally, the viral vector comprises a polynucleotide sequence encoding GLP-1 (glucagon like peptide 1);
    (g) wherein, optionally, the viral vector is encompassed by a mammalian cell.

In a further preferred embodiment, the present invention provides a composition, preferably a pharmaceutical composition, comprising at least one compound of the invention, optionally in combination with a gene therapeutic expression system for GLP-1 and/or GIP according to any one of the embodiments of the present invention mentioned above wherein
  the signal sequence upstream of the gene of interest (GLP-1; GIP) is the murine immunoglobulin κ signal sequence or the glia monster exendin signal sequence; and/or
  the polyadenylation signal downstream of the gene of interest (GLP-1; GIP) is derived from simian virus 40 (SV 40); and/or
  the proteolytic cleavage site is cleaved by furin protease; and/or
  the gene delivery vector for expression the gene of interest is an adenoviral, retroviral, leniviral, adeno associated viral vector; and/or the constitutive promoter is a cytomegalovirus (CMV) promoter, or a Rous sarcoma long-terminal repeat (LTR) sequence, and the SV 40 early gene gene promoter; and the inducible promoter is the Tet-On™/Tet-Off™ system available from Clontech.

Furthermore, the compositions or pharmaceutical compositions according to any one of the embodiments described above comprise additionally at least one customary carrier and/or excipient.

Galenic Preparations and Formulations

Compounds of the invention are preferably presented as pharmaceutical compositions which comprise a compound of the invention together with one or more pharmaceutically acceptable diluents or carriers.

Preferably these compositions are in unit dosage forms from such as tablets, pills, capsules, powders, granules, sterile parenteral solutions or suspensions, metered aerosol or liquid sprays, drops, ampoules, autoinjector devices or suppositories. The compound may be administered to a patient by any conventional route of administration, including, but not limited to, intravenous, oral, subcutaneous, intramuscular, intradermal, parenteral, intranasal, sublingual or rectal administration, or for administration by inhalation or insufflation.

Compounding techniques: To prepare the pharmaceutical compositions of this invention, one or more compounds of the present invention, specifically the DP IV inhibitors according to formula 1, as well as optionally, other agents as described for the "pharmaceutical combinations", and their corresponding pharmaceutically acceptable acid addition salt forms, as the active ingredients, are intimately admixed with a pharmaceutical carrier according to conventional pharmaceutical compounding techniques, which carrier may take a wide variety of forms depending of the form of preparation desired for administration. Compounds of the present invention may also be coupled with soluble polymers as targetable drug carriers.

Homogeneous preparation: For preparing solid compositions such as tablets, the principal active ingredient is ideally mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is ideally dispersed evenly throughout the composition so that the composition may be readily subdivided into equally effective dosage forms such as tablets, pills and capsules. This solid preformulation composition may then be subdivided into unit dosage forms of the type described above containing from about 0.1 to about 1000 mg, preferably from about 5 to about 500 mg of the active ingredient of the present invention.

Concentration and content of active agent: The pharmaceutical compositions herein will contain, per dosage unit, e.g. tablet, capsule, powder, injection, suppository, teaspoonful and the like, of from about 0.01 mg to about 1000 mg (preferably about 5 to about 500 mg) and may be given at a dosage of from about 0.1 to about 50 mg/kg bodyweight per day (preferably 1 to 50 mg/kg per day).

Oral dosage forms: In preparing the compositions in oral dosage form, any of the usual pharmaceutical media may be employed. Compositions suitable for oral administration include solid forms, such as pills, tablets, caplets, capsules (each including immediate release, timed release and sustained release formulations), granules, and powders. For solid oral preparations such as, for example, powders, capsules, gelcaps and tablets, suitable carriers and additives may advantageously include starches, sugars, diluents, granulating agents, lubricants, binders, disintegrating agents and the like. More preferably, for oral administration in the form of a tablet or capsule, the active drug component can be combined with an oral, non-toxic pharmaceutically acceptable inert carrier such as ethanol, glycerol, water and the like.

Coating of tablets, pills and capsules: Because of their ease in administration, tablets, pills and capsules represent the most advantageous oral dosage unit form, in which case solid pharmaceutical carriers are employed. If desired, the tablets, pills or capsules of the novel composition can be advantageously sugar coated or enteric coated by standard techniques or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

The liquid forms in which the novel compositions of the present invention may be advantageously incorporated for administration orally or by injection include aqueous solutions, suitably flavoured syrups, elixirs, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin. The liquid forms are suitable in flavored suspending or dispersing agents such as the synthetic and natural gums, for example, tragacanth, acacia, methyl-cellulose and the like. Isotonic preparations which generally contain suitable preservatives are employed when intravenous administration is desired.

For liquid oral preparations, such as for example, suspensions, elixirs and solutions, suitable carriers and additives may advantageously include water, glycols, oils, alcohols, flavoring agents, preservatives, coloring agents and the like.

Forms useful for parenteral administration include sterile solutions, emulsions and suspensions. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. For parenteral administration, sterile suspensions and solutions are desired. The pharmaceutical compositions herein will contain, per dosage unit, e.g. solution, suspension, emulsion, injection, teaspoonful and the like, an amount of the active ingredient necessary to deliver an effective dose as described above.

Depot formulations for intramuscular injection: Alternatively, the composition may be presented in a form suitable for once-weekly or once-monthly administration; for example, an insoluble salt of the active compound, such as the decanoate salt, may be adapted to provide a depot preparation for intramuscular injection.

Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen and dosage strength will need to be accordingly modified to obtain the desired therapeutic effects.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines using processes well described in the art.

Compounds of this invention may be administered in any of the foregoing compositions and according to dosage regimens established in the art whenever treatment of the addressed disorders is required.

Dosage Regimen and Strength:

Advantageously, compounds of the present invention may be administered in a single daily dose, or the total daily dosage may be administered in divided doses of two, three or four times daily.

The daily dosage of the products may be varied over a wide range from 0.01 to 1.000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.1 mg/kg to about 50 mg/kg of body weight per day. Preferably, the range is from about 1 to about 50 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, bioavailability due to the mode of administration, and the advancement of disease condition. In addition, factors associated with the particular patient being treated, including patient age, weight, diet and time of administration, should generally be considered in adjusting dosages.

The dosages, however, may be varied depending upon the requirement of the patients, the severity of the condition being treated and the compound being employed. The use of either daily administration or post-periodic dosing may be employed. Typically the dosage will be regulated by the physician based on the characteristics of the patient, his/her condition and the therapeutic effect desired.

The compounds or compositions of the present invention may be taken before a meal, while taking a meal or after a meal. When taken before a meal the compounds or composition of the present invention an be taken 1 hour, preferably 30 or even 15 or 5 minutes before eating. When taken while eating, the compounds or compositions of the present invention can be mixed into the meal or taken in a separate dosage form as described above. When taken after a meal, the compounds or compositions of the present invention can be taken 5, 15 or 30 minutes or even 1 hour after finishing a meal.

EXAMPLES OF THE INVENTION

Chemical Synthesis

Scheme 1: Boronates

Boronates may be prepared according to the following example scheme:

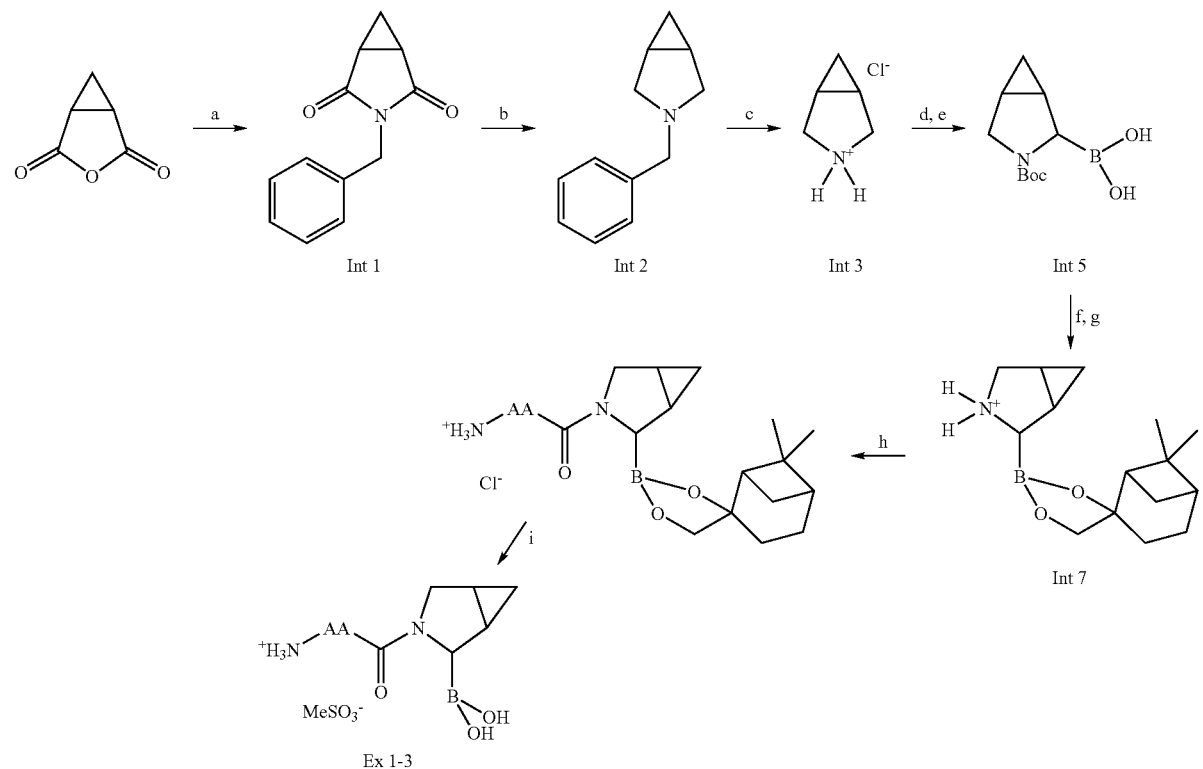

Reagents and conditions: a: benzylamine, 180° C., 2 h; b: Sodium bis(2-methoxyethoxy)aluminumhydride (RED-Al®), ether, 30 min, c: Pd/C, H₂, 10 bar r.t., 21 h then HCl (gaseous); d:Boc₂O, NaOH, r.t., 24 h; e: TMEDA, secBuLi, B(OMe)₃, −70° C. 3 h, then r.t., 24 h; f: (1S,2S,3R,5S)-pinanediole, ether, r.t. 2 h; g: HCl/ether, r.t., 5 min; h: Boc-Pro-OH, EDC, HOBt, NMM, 0° C., then r.t. 24 h, then HCl/ether; r.t., 5 min; i: DOWEX® ion-exchanger, then MeSO₃H,
AA stands for "amino acid"

Scheme 2: Phosphonates

Phosphonates may be prepared according to the following example scheme:

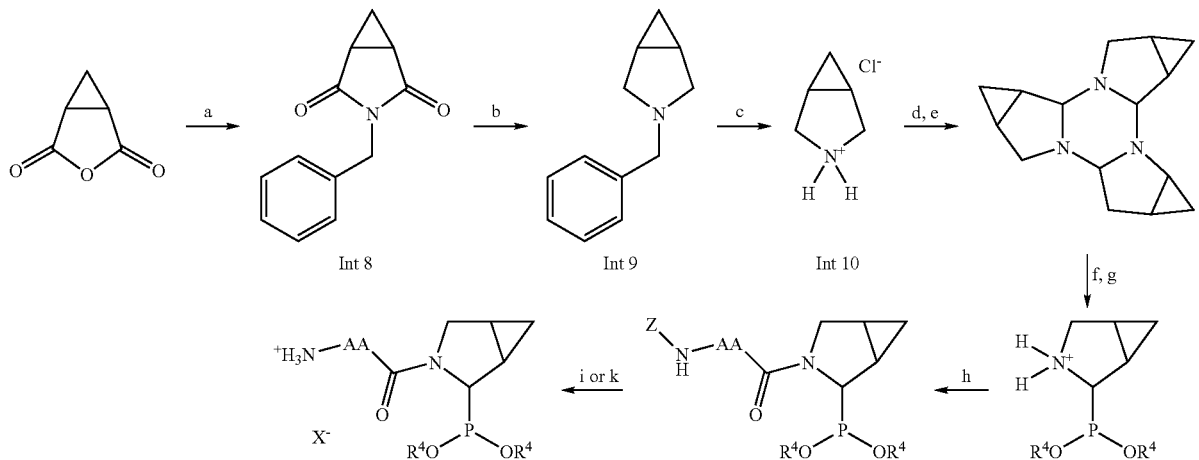

Reagents and conditions: a: benzylamine, 180° C., 2 h; b: RED-Al®, ether, 30 min, c: Pd/C, H₂, 10 bar r.t., 21 h then HCl (gaseous); d:TEA, methylenechloride e: sodiumperoxodisulfate, AgNO₃, 0° C. 2 h; f: HPO(OR⁴)₂, 85° C., 5 h g: HCl/ether, r.t., 5 min; h: Z-AA-OH, EDC, HOBt, NMM, 0° C., then r.t. 24 h, i: PdC/H₂, then HCl/dioxane, k: 30% HBr/AcOH AA stands for "amino acid". X⁻ represents a suitable halide ion.

Synthesis of Examples

Materials and Equipment

Materials: cis-1,2-cyclopropanedicarboxylic acid anhydride, benzylamine, diboc, TMEDA, s-BuLi, methansulfonic acid, phenylboronic acid 1S,2S,3R,5S pinane-1,2-diol, RED-Al® were purchased from ALDRICH CO. Boc-Proline was purchased from BACHEM.

ESI-Mass spectra were obtained with a SCIEX API 365 spectrometer (Perkin Elemer). The ¹H-NMR (500 MHz) data were recorded on a BRUKER AC 500, using D₂O as solvent. Silica gel (for flash chromatography, MERCK) was used for column chromatography. All solvents were distilled and dried prior use.

Experimental Procedure 3-(Benzyl)-3-azabicyclo(3.1.0)hexan-2,4-dione (Int 1)

Benzylamine (8.8 mmol, 9.97 ml) was added dropwise to ice cooled cis-1,2-cyclopropanedicarboxylic acid anhydride (8.8 mmol, 0.99 g). After that the mixture was heated to 180° C. for 2 h on an oil bath. After cooling to r.t. the resulting solid oil was recrystallised from isopropanol.

Yield: 1.6 g (90%), MS: 202.22 (M+H).

3-Benzyl-3-azabicyclo(3.1.0)hexane (Int 2)

RED-Al® (65% in toluene) (36.1 mmol, 7.29 g) was dissolved in absolute diethylether (20 ml) and cooled down to 0° C. under an argon atmosphere. Int 1 (1.6 g, 7.95 mmol) was added. The mixture was stirred at 0° C. for 30 min and stirred under reflux for an additional 3 h. The workup was done by adding water (10 ml) to the cooled solution and filtering through celite. After that the phases were separated. The organic phase was dried (MgSO₄) and evaporated, yielding a yellowish oil which was used further without purification.

Yield: 1.37 g (90%), MS: 174.3 (M+H).

3-Azabicyclo(3.1.0)hexane*HCl (Int 3)

Int 2 (28.6 mmol, 4.95 g) was dissolved in ethanol (20 ml) and Pd/C (150 mg) was added. The mixture was placed in a pressure secure vessel and hydrogen was filled up to a pressure of 10 bar. The hydrogenation was performed for 21 h at r.t., then the catalyst was filtered off and gaseous dry hydrochloric acid was led into the solution until saturation was reached. After that, dry diethyl ether (30 ml) was added. The resulting precipitate was filtered off and dried under vacuo.

Yield: 3.196 g, MS: 120.6 (M+H).

3-N-t-butyl-oxy-carbonyl-azabicyclo(3.1.0)hexane (Int 4)

Int 3 (4.18 mmol, 0.5 g) was dissolved in a mixture of dioxane/water 1/1 (v/v) (15 ml). 1N NaOH (8.36 ml) and Boc₂O (8.36 mmol, 1.00 g) were added. The mixture was stirred overnight at r.t. After that the dioxane was evaporated and the aqueous phase was extracted with petroleum ether (3×30 ml). The organic phase was dried and evaporated. The resulting oil was purified by means of column chromatography using an n-heptane/CHCl₃ gradient.

Yield: 660 mg, MS: 128 (M-tBu), 184 (M+H).

3-(t-Bu-oxy-carbonyl)-3-azabicyclo(3.1.0)hexan-2-yl-2-boronic acid (Int 5)

TMEDA (6.55 mmol, 0.988 ml) was dissolved in absolute ether (30 ml) and the mixture was cooled down to −70° C. Int 4 (3.27 mmol, 600 mg) dissolved in absolute ether (5 ml) was added dropwise. After 10 min of stirring secBuLi (1.3M in cyclohexane) (3.93 mmol, 3.02 ml) was added dropwise over 1 h. After stirring over 3 h at −65 to −50° C. boronic acid trimethylester was added and stirring was continued overnight at r.t.

The workup was done by quenching with water (2 ml) and adding 2N NaOH (50 ml). The phases were separated and the aqueous phase was brought to pH 2 by adding 2N HCl (65 ml) and subsequently extracted by means of ethyl acetate (50 ml). After drying the solvent was evaporated and the product was yielded as a colorless glass.

Yield: 426 mg, MS: 228.2 (M+H), 172.3, 154.2.

3-(t-Bu-oxy-carbonyl)-3-azabicyclo(3.1.0)hexan-2-yl-2-boronic acid (1S,2S,3R,5S)-pinandiole ester (Int 6)

Int 5 (1.76 mmol, 400 mg) was dissolved in absolute ether (20 ml). (1S,2S,3R,5S)-pinandiole was added into the stirred solution. After 2 h of stirring at r.t. the solvent was evaporated.

Yield: 629 mg, MS 362.3 (M+H).

(1S,2S,3R,5S)-pinandiole 3-azabicyclo(3.1.0)hexan-2-yl-2-boronate (Int 7)

To Int 6 (620 mg, 1.71 mmol) HCl in ether (saturated solution) (20 ml) was added. The resulting precipitate was filtered off and dried over $P_2O_5$.

Yield: 350 mg, MS: 262.3 (M+H).

3-(α-Aminoacyl)-(1S,2S,3R,5S)-pinandiole 3-azabicyclo(3.1.0)hexan-2-yl-2-boronates*HCl A Boc-protected amino acid (1.24 mmol) was dissolved in dry methylenechloride (8 ml). After cooling to 0° C. HOBt (168 mg, 1.24 mmol) and EDC (1.616 mmol, 309.8 mg) were added. Then the solution was stirred for 30 min a 0° C. and NMM (2.46 mmol, 274 µl) and Int 7 (1.24 mmol, 370 mg) were added. The mixture was stirred overnight and the workup was done by extracting with $KHSO_4$-solution, $NaHCO_3$ solution and brine. After that the organic layer was separated, dried and the resulting oil was dissolved in a saturated solution of HCl in ether and cooled to 0° C. The resulting precipitate was filtered off and dried over $P_2O_5$.

3-(α-Aminoacyl)-(3.1.0)hexan-2-yl-2-boronates*$MeSO_3$ (Examples 1-3)

A 3-(α-Aminoacyl)-(1S,2S,3R,5S)-pinandiole-3-azabicyclo(3.1.0)hexan-2-yl-2-boronate*HCl (1.046 mmol) was dissolved in water (10 ml). The pH was adjusted to 2 by adding 2N HCl. After the addition of phenyl boronic acid (1.07 mmol, 134 mg) and heptane (15 ml), the mixture was stirred at r.t. The heptane layer was exchanged by fresh heptane and this procedure was repeated 5 times every 20 min. The aqueous phase was applied on an ion-exchange column (DOWEX® 50) and eluted using a solution of 0.5N ammonia. After lyophilisation the remaining 200 mg of the remaining glass were dissolved in absolute methanol (7 ml). Methanesulfonic acid (0.884 mmol, 57.4 µl) acid was dissolved in methanol (0.5 µl) and added to the stirred solution. After stirring for 3 h at r.t. the solvent was removed and the remaining glass was triturated and diethyl ether to give a white amorphous powder.

3 examples were prepared as follows:

| Example | $R^1$* | $R^2$ | $R^3$ | Z |
|---|---|---|---|---|
| 1 | L-CHMe$_2$ | H | H | B(OH)$_2$ |
| 2 | L-CMe$_3$ | H | H | B(OH)$_2$ |
| 3 | L-CHMeCH$_2$Me | H | H | B(OH)$_2$ |

*L indicates that the amino acid moiety has L stereochemistry

Biological Testing

Compounds may be tested for biological activity in a number of assays:

Example 1

Determination of $IC_{50}$-Values of DP IV, DP II and DP9 Inhibition

100 µl inhibitor stock solution were mixed with 100 µl buffer (HEPES pH 7.6) and 50 µl substrate (Gly-Pro-pNA, final concentration 0.4 mM) and preincubated at 30° C. Reaction was started by addition of 20 µl enzyme solution (either purified porcine DP IV, human recombinant DP IV, human recombinant DP II or human recombinant DP9). Formation of the product pNA was measured at 405 nm over 10 min using the HTS 7000Plus plate reader (Perkin Elmer) and slopes were calculated. The final inhibitor concentrations ranged between 1 mM and 30 nM.

For calculation of $IC_{50}$-values GraFit 4.0.13 (Erithacus Software) was used.

Results:

| Example | AA | MS (M + H) | NMR ($^1$H, $^{13}$C) | $IC_{50}$ (DP IV porcine, kidney) (mol/L) | $IC_{50}$ (DP IV human, recombinant) (mol/L) | $IC_{50}$ (DP II human, recombinant) (mol/L) | $IC_{50}$ (DP9 human, recombinant) (mol/L) |
|---|---|---|---|---|---|---|---|
| 1 | Val | 227.08 | confirms | 3.53E−9 | 3.16E−08 | 3.82E−06 | 1.59E−08 |
| 2 | tBuGly* | 241.16 | confirms | 1.02E−8 | 7.50E−08 | 2.11E−05 | 1.84E−08 |
| 3 | Ile | 241.61 | confirms | 9.46E−9 | 4.51E−08 | 1.47E−06 | 1.08E−08 |

*amino acid tBuGly is:

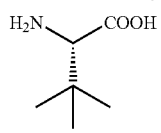

Example 2

Anti-Metastatic Effect of Compounds of Formula 1

The compounds of the present invention may be tested according to the following test protocol:

Materials and Methods

Animals, Injection of Tumor Cells and Processing of Lungs

In F344/Ztm rats two different assays may be performed:
(1) In vivo adhesion assay based on quantification of CFSE labeled tumor cells in lung tissue 1 h after inoculation; and
(2) In vivo lung colonization assay based on quantification of metastatic nodules on lung surface 2 weeks after inoculation.

Animals can be obtained from a breeding colony at the Central Animal Laboratory at Hannover Medical School, Germany and maintained in a specific-pathogen-free facility at 25° C. under a 12 h light-12 h dark cycle (light on at 07.00 h), with ad libitum access to food and water. The number of animals per experiment should be at least six male animals per condition and time point.

Cell culture, injection of tumor cells, dissection of the animals and immunohistochemistry are to be conducted as follows: $1*10^6$ MADB106 tumor cells derived from log phase of tumor growth will be injected via the lateral tail vein and lungs removed at different time points thereafter. For in situ quantification of tumor cells at early time points after injection (30 min), cells will be vital dye stained using the fluorescein derivate 5-(and -6)-carboxyfluorescein diacetate succinimidyl ester (CFSE; Molecular Probes, Eugene, Oreg., USA) before injection. For quantification of lung surface colonies at later time points (2 weeks after tumor cell inoculation), en-bloc dissected lungs and the heart hate to be injected with 8 ml Bouin's solution (72% saturated picric acid solution, 23% formaldehyde, and 5% glacial acetic acid) and fixed in the same solution until lung surface nodules can be counted (see below).

Implantation of Osmotic Minipumps for Chronic Intragastric Infusion of Compounds Osmotic minipumps (Alzet model 2ML4; flow rate, 2.5 µl/hr; Alza Corporation), administering a constant supply of the different compounds, aseptically prefilled with either saline+DMSO, or DPIV inhibitor dissolved in saline+DMSO, attached to a cannula via polyethylene tubing, and prewarmed in 0.9% NaCl at 37° C. for 4 hr, have to be placed subcutaneously in the abdominal area. The cannula should be implanted intragastrically with a heating-induced enlarged tip of the cannula in the lumen of the gaster.

Experiments

Two experiments, a) and b), with five groups each can be conducted.

Mode of Treatment a) Single ip–1 h+iv injection for quantification of early effects 30 min after tumor inoculation,
b) Chronic infusion via implanted Alzet-pumps and intragastric tubing Dose Groups 1. Treatment group, receiving compound of formula 1
2. Control group, receiving in a) Saline+DMSO, in b) (SHAM-controls): SHAM Dosages a) Single ip+iv injection of 1.5 µmol/kg/24 h
Infusion of 1.5 mmol/24 h over 16 days via minipumps Animals/Group 6-7 adult male F344/Ztm rats.

Read Outs a) Number of CFSE positive cells in lung tissue
b) Number of lung surface metastasis and body weight change Experimental Design a) one set of 30 animals with n=6 animals/group.
b) one set of 32 animals with n=6-7 animals/group equipped with drug-loaded miniosmotic pumps.

Immunohistochemistry for CFSE-Labeled Tumor Cells

Immunostaining of CFSE-labeled MADB106 tumor cells is achieved using mAbs characterizing the intracellular CFSE antigen (anti-CFSE; mAb DE1, Boehringer, Mannheim, Germany; mouse, 1:100). For immunohistochemistry, one or two consecutive APAAP stainings should be performed as previously described (von Hörsten et al., 2000) In brief, 8 µm cryostat sections are incubated with the primary antibodies for 30 min at room temperature. Sections are washed with TBS-Tween followed by incubation for 30 min with the bridging antibody (100 □l Dako Z 0259, 1/50, rabbit anti-mouse, Dako, Hamburg, Germany) diluted in 5% rat serum. After another rinse the APAAP complex (100 □l Dako D 0651, 1/50, mouse; in TBS-Tween) is added and the sections are incubated for 30 min followed by addition of the substrate Fast Blue (Sigma, Deisenhofen, Germany). The incubation with primary antibody (i.e.: 3.2.3 or DE 1) is performed subsequently for 45 min at room temperature followed by an identical procedure except that Fast Red (Sigma) was the substrate. Finally, sections are counterstained with hematoxylin. Control sections are included in which one or both primary antibodies were omitted.

Quantification of Tumor Targets: In Vivo/In Situ Cell Adhesion Assay

Lungs are collected at 30 min after the i.v. inoculation of $1*10^6$ MADB106 tumor cells) and injection of 500 µl saline instead of tumor cells is used as a vehicle control. CFSE labeling of MADB106 cells allows the quantification of tumor cells in lung tissue in situ (von Hörsten et al., 2000). The assessment of DE1+tumor cells and effector cells in lung tissue is carried out using image analysis approach. All CFSE-labeled MADB106 tumour cells and leukocyte subsets within a grid on the ocular lens are counted (Zeiss Kpl-W 12.5×; grid 0.75×0.75 mm=0.5625 mm²/grid, using a Zeiss Neofluar objective, ×10, NA=0.3). Each right upper lobe of the lungs is sectioned at 6 randomly chosen non-adjacent levels. From each level, three sections should be evaluated. On average, 30 grid numbers per section should be examined (i.e. 0.5625 mm²/grid×30 grids×3 sections×6 levels) resulting in an area per animal of 3.04 cm².

Statistical Analysis

Data are analyzed by one-way analyses of variance (ANOVA) (factor: "treatment") followed by Fisher's PLSD post hoc tests, if appropriate. All data are presented as means±S.E.M.

Example 3

Determination of DP IV Inhibiting Activity of the Compounds of Formula 1 after Intravasal and Oral Administration to Wistar Rats The compounds of the present invention may be tested according to the following test protocol:

Animals

Male Wistar rats (Shoe: Wist(Sho)) with a body weight ranging between 250 and 350 g can be purchased from Tierzucht Schönwalde (Schönwalde, Germany).

Housing Conditions

Animals should be single-caged under conventional conditions with controlled temperature (22±2° C.) on a 12/12 hours light/dark cycle (light on at 06:00 AM). Standard pelleted chow (Ssniff® Soest, Germany) and tap water acidified with HCl were allowed ad libitum.

Catheter Insertion into Carotid Artery

After ≧one week of adaptation at the housing conditions, catheters are implanted into the carotid artery of Wistar rats under general anaesthesia (i.p. injection of 0.25 ml/kg b.w. Rompun® [2%], BayerVital, Germany and 0.5 ml/kg b.w. Ketamin 10, Atarost GmbH & Co., Twistringen, Germany). The animals should be allowed to recover for one week. The catheters are flushed with heparin-saline (100 IU/ml) three times per week.

In case of catheter dysfunction, a second catheter can be inserted into the contra-lateral carotid artery of the respective rat. After one week of recovery from surgery, this animal can then be reintegrated into the study. In case of dysfunction of the second catheter, the animal has to be withdrawn from the study. A new animal has to be recruited and the experiments can be continued in the planned sequence, beginning at least 7 days after catheter implantation.

Experimental Design

To rats with intact catheter function are administered placebo (1 ml saline, 0.154 mol/l) or 100 mg/kg b.w. of the compound of the general formula (1) via the oral and the intra-vasal (intra-arterial) route.

After overnight fasting, 100 µl samples of heparinised arterial blood are collected at −30, −5, and 0 min. The test substance is dissolved freshly in 1.0 ml saline (0.154 mol/l) and is administered at 0 min either orally via a feeding tube (75 mm; Fine Science Tools, Heidelberg, Germany) or via the intra-vasal route. In the case of oral administration, an additional volume of 1 ml saline is injected into the arterial catheter. In the case of intra-arterial administration, the catheter is immediately flushed with 30 µl saline and an additional 1 ml of saline is given orally via the feeding tube.

After application of placebo or the test substances, arterial blood samples will be collected at 2.5, 5, 7.5, 10, 15, 20, 40, 60 and 120 min from the carotid catheter of the conscious unrestrained rats. All blood samples are collected into ice cooled Eppendorf tubes (Eppendorf-Netheler-Hinz, Hamburg, Germany) filled with 10 µl 1M sodium citrate buffer (pH 3.0) for plasma DP IV activity measurement. Eppendorf tubes are centrifuged immediately (12000 rpm for 2 min, Hettich Zentrifuge EBA 12, Tuttlingen; Germany): The plasma fractions are stored on ice until analysis or can be frozen at −20° C. until analysis. All plasma samples should be labelled with the following data:

Code number
Animal Number
Date of sampling
Time of sampling

Analytical Methods

The assay mixture for determination of plasma DP IV activity consists of 80 µl reagent and 20 µl plasma sample. Kinetic measurement of the formation of the yellow product 4-nitroaniline from the substrate glycylprolyl-4-nitroaniline is performed at 390 nm for 1 min at 30° C. after 2 min pre-incubation at the same temperature. The DP IV activity is expressed in mU/ml.

Statistical Methods

Statistical evaluations and graphics can, e.g. be performed with PRISM® 3.02 (GraphPad Software, Inc.). All parameters are analysed in a descriptive manner including mean and SD.

Compounds and combinations of the invention may have the advantage that they are, for example, more potent, more selective, have fewer side-effects, have better formulation and stability properties, have better pharmacokinetic properties, be more bioavailable, are more compatible or effective in combination with other drugs or be more readily synthesized than other compounds of the prior art.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned above are herein incorporated in their entirety by reference.

The invention embraces all combinations of preferred and more preferred groups and embodiments of groups recited above.

LITERATURE von Hörsten S, Helfritz A, Kuhlmann S, Nave H. Tschernig T. Pabst R, Ben-Elyahu S, Meyer D, Schmidt R E, Schmitz C (2000) Stereological quantification of carboxyfluorescein-labeled rat lung metastasis: a new method for the assessment of natural killer cell activity and tumor adhesion in vivo and in situ. J Immunol Meth 239: 25-34

ABBREVIATIONS

AA amino acid

ADA American Diabetes Association

AIDS acquired immune deficiency syndrome

AMC aminomethyl coumarine

ANOVA analysis of variance

APAAP alkaline phosphatase-anti-alkaline phosphatase

Boc/BOC t-butyloxycarbonyl

CFSE carboxyfluorescein succinimidyl ester

CMV cytomegalovirus diboc di-tert-butyl dicarbonate

DMSO dimethyl sulfoxide

DNA deoxyribonucleic acid

DPP dipeptidyl peptidase

DPRP dipeptidyl peptidase IV-related protein EDC ethylcarbodiimide

EGF epidermal growth factor

Fisher's PLSD Fisher's protected-least-significant-difference test

FU fluorouracil

GIP gastric-inhibitory peptide

GLP-1 glucagon-like peptide 1

HEPES 4-(2-hydroxyethyl)-1-piperazineethanesulfonic acid

HIV human immunodeficiency virus

HLA human leukocyte antigen

HMG-CoA hydroxamethylglutaryl-Coenzyme A

HNF 1 hepatocyte nuclear factor 1

HOBt hydroxybenzotriazole

HPLC high performance liquid chromatography

IDDM insulin-dependent diabetes mellitus

IFG impaired fasting glucose

IGM impaired glucose metabolism

IGT impaired glucose tolerance

LTR long-term repeat min minute

MODY maturity-onset diabetes of the young

NGT normal glucose tolerance

NIDDM non-insulin-dependent diabetes mellitus

NMM N-methylmorpholine

OGTT oral glucose tolerance test

PACAP pituitary adenylate cyclase activating polypeptide

PDX pyruvate dehydrogenase protein X pNA para-nitroaniline

PPAR peroxisome proliferator-activated receptor

PTP-1B protein tyrosin phosphate IB r.t. room temperature

SV40 simian virus 40

TCF 1 transcription factor 1

TEA triethanolamine

TMEDA Tetramethylethylenediamine

VGF vaccinia growth factor

WHO World Health Organization

The invention claimed is:

1. A compound of formula (I):

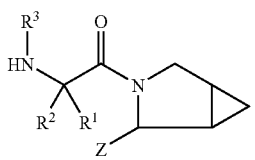

wherein
R$^1$ and R$^2$ are independently selected from hydrogen, alkyl, alkenyl, alkynyl, cycloalkyl, alkylcycloalkyl, heterocyclyl, carbocyclyl, aryl, -alkylaryl, heteroaryl-alkylheteroaryl and an amino acid or a peptide residue;
R$^3$ represents hydrogen;

Z is a group of formula I or II:

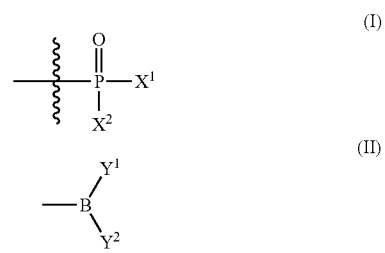

wherein X$^1$ and X$^2$ independently represent OR$^4$;
R$^4$ is selected from the group consisting of hydrogen; alkyl, alkenyl, alkynyl, cycloalkyl any of which aforementioned four groups may optionally be substituted by hydroxy; heterocyclyl, carbocyclyl, aryl, -alkylaryl, heteroaryl and -alkylheteroaryl;
Y$^1$ and Y$^2$ are independently selected from hydroxy, alkoxy, cycloalkyloxy, aryloxy and heteroaryloxy; or
Y$^1$ and Y$^2$ are connected to form one of the following cyclic boronic diester groups:

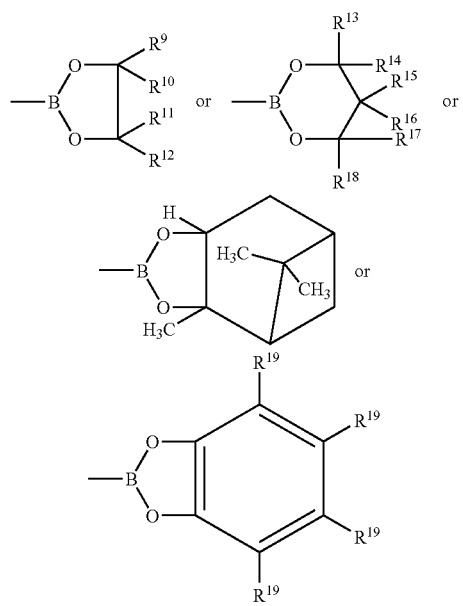

wherein
R$^9$-R$^{18}$ are independently hydrogen, alkyl, cycloalkyl or aryl; and
each R$^{19}$ group is independently selected from hydrogen, alkyl, aryl, halo, alkoxy, aryloxy, thioalkyl and thioaryl;
when Z represents a group of formula (I):

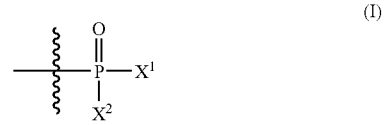

then R$^3$ may also represent alkyl, alkenyl, alkynyl, cycloalkyl, alkylcycloalkyl, heterocyclyl, carbocyclyl, aryl, -alkylaryl, -alkylheteroaryl, an amino acid or a peptide residue; and when Z represents a group of formula (I) $R^1$ and $R^3$ may also optionally be connected to form a ring of the structure of formula (III)

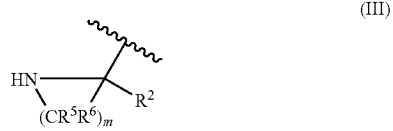

wherein m is an integer in the range of 2 to 6;
$R^2$ is as defined above; and
$R^5$ and $R^6$ are independently selected from hydrogen, hydroxy, alkoxy, alkyl, alkenyl, alkynyl, cycloalkyl, halo, amino, substituted amino, carbocyclyl, aryl, arylalkyl-, heteroaryl, heteroarylalkyl-, heterocyclyl, alkylcarbonylamino-, arylcarbonylamino-, alkoxycarbonylamino-, aryloxycarbonylamino-, alkoxycarbonyl-, aryloxycarbonyl-, and alkylaminocarbonylamino-;
including all stereoisomers and pharmaceutically acceptable salts thereof.

2. A compound according to claim 1, wherein Z is a group of formula (I).

3. A compound according to claim 1, wherein $R^4$ represents hydrogen, lower alkyl or a substituted phenyl ring.

4. A compound according to any one of claims 1 to 3, wherein $R^1$, $R^2$ and $R^3$ independently represent hydrogen, alkyl, alkylcycloalkyl or cycloalkyl.

5. A compound according to claim 1 wherein Z is a group of formula (II).

6. A compound according to claim 1, wherein $Y^1$ and $Y^2$ represent OH.

7. A compound of any one of claims 1, wherein $R^2$ is hydrogen.

8. A compound of any one of claims 1, wherein $R^1$ represents $C_2$-$C_6$ alkyl.

9. A compound according to claim 8, wherein $R^1$ represents $CMe_3$, $CHMe_2$ or $CHMeCH_2Me$.

10. A compound according to claim 9, wherein the moiety $HR^3N$—$CR^1R^2$—CO— represents the residue of L-valine, L-isoleucine or L-(t-butyl)glycine.

11. A compound according to claim 1, wherein $R^1$, $R^2$, $R^3$, and Z are defined in the following table,

| Example | $R^1$ * | $R^2$ | $R^3$ | Z |
|---|---|---|---|---|
| 1 | L-$CHMe_2$ | H | H | $B(OH)_2$ |
| 2 | L-CMe | H | H | $B(OH)_2$ |
| 3 | L-$CHMeCH_2Me$ | H | H | $B(OH)_2$ |

* L indicates that the amino acid moiety has L stereochemistry or a pharmaceutically acceptable salt thereof.

12. A pharmaceutical composition comprising at least one compound according to claim 1 optionally in combination with at least one therapeutically acceptable carrier and/or excipient.

13. The pharmaceutical composition according to claim 12 for parenteral, enteral or oral administration.

14. The pharmaceutical composition of claim 12, which comprises additionally at least one anti-tumor drug selected from the group consisting of cytotoxins and agents such as antimetabolites, alkylating agents, anthracyclines, antibiotics, antimitotic agents, procarbazine, hydroxyurea, asparaginase, corticosteroids, mytotane (O,P1-(DDD)), interferons and radioactive agents.

15. The pharmaceutical composition of claim 12, which comprises additionally at least one anti-diabetic agent.

16. The pharmaceutical composition of claim 12, which comprises additionally at least one agent selected from the group consisting of
(a) other DP IV inhibitors
(b) insulin sensitizers selected from the group consisting of
  (i) PPAR agonists,
  (ii) biguanides, and
  (iii) protein tyrosin phosphatase-1B (PTP-1B) inhibitors;
(c) insulin and insulin mimetics;
(d) sulfonylureas and other insulin secretagogues;
(e) α-glucosidase inhibitors;
(f) glucagon receptor agonists;
(g) GLP-1; GLP-1 mimetics, e.g. N,N-2211 (liraglutide), and GLP-1 receptor agonists;
(h) GLP-2; GLP-2 mimetics, e.g. ALX-0600 (teduglutide) and GLP-2 receptor agonists;
(i) exendin-4 and exendin-4 mimetics, e.g. exenatide (AC-2993, synthetic exendin-4);
(j) GIP, GIP mimetics, and GIP receptor agonists;
(k) PACAP, PACAP mimetics, and PACAP receptor 3 agonists;
(l) cholesterol lowering agents selected from the group consisting of
  (i) HMG-CoA reductase inhibitors,
  (ii) sequestrants,
  (iii) nicotinyl alcohol, nicotinic acid and salts thereof,
  (iv) PPARα agonists,
  (v) PPARα/γ dual agonists,
  (vi) inhibitors of cholesterol absorption,
  (vii) acyl CoA:cholesterol acyltransferase inhibitors, and
  (viii) antioxidants;
(m) PPARδ agonists;
(n) antiobesity compounds;
(o) an ileal bile acid transporter inhibitor; and
(p) anti-inflammatory agents.

17. The pharmaceutical composition of claim 12, which further comprises a gene therapeutic expression system for GLP-1 comprising at least one of:
(i) a viral vector comprising
  (a) a polynucleotide sequence encoding GLP-1 (glucagon like peptide-1);
  (b) a polynucleotide sequence encoding a signal sequence upstream of (a);
  (c) a polyadenylation signal downstream of (a); and
  (d) a polynucleotide sequence encoding a proteolytic cleavage site located between the polynucleotide sequence encoding GLP-1 and the polynucleotide sequence encoding the signal sequence;
wherein
  the expression of GLP-1 underlies a constitutive promoter or is controlled by a regulatable promoter;
  optionally, the viral vector comprises a polynucleotide sequence encoding GIP (glucose dependent insulinotropic peptide);
  optionally, the viral vector is encompassed by a mammalian cell; and (ii) a gene therapeutic expression system for GIP comprising a viral vector comprising
  (a) a polynucleotide sequence encoding GIP (glucose dependent insulinotropic peptide);
  (b) a polynucleotide sequence encoding a signal sequence upstream of (a);
  (c) a polyadenylation signal downstream of (a); and
  (d) a polynucleotide sequence encoding a proteolytic cleavage site located between the polynucleotide sequence encoding GIP and the polynucleotide sequence encoding the signal sequence;
  wherein
    the expression of GIP underlies a constitutive promoter or is controlled by a regulatable promoter;
    optionally, the viral vector comprises a polynucleotide sequence encoding GLP-1 (glucagon like peptide 1); and
    optionally, the viral vector is encompassed by a mammalian cell.

18. The pharmaceutical composition of claim 17, wherein at least one of the following conditions are satisfied:
  the signal sequence upstream of the gene of interest (GLP-1; GIP) is the murine immunoglobulin κ signal sequence or the glia monster exendin signal sequence;
  the polyadenylation signal downstream of the gene of interest (GLP-1; GIP) is derived from simian virus 40 (SV 40);
  the proteolytic cleavage site is cleaved by furin protease;
  the gene delivery vector for expression the gene of interest is an adenoviral, retroviral, leniviral, adeno associated viral vector; and
  the constitutive promoter is a cytomegalovirus (CMV) promoter, or a Rous sarcoma long-terminal repeat (LTR) sequence, and the SV 40 early gene gene promoter; and the inducible promoter comprises a tetracycline-resistance operon.

* * * * *